(12) United States Patent
Lindars et al.

(10) Patent No.: US 11,273,428 B2
(45) Date of Patent: Mar. 15, 2022

(54) VAPORIZABLE SUBSTANCE STORAGE DEVICE

(71) Applicant: Iconic Ventures, Inc., Portland, OR (US)

(72) Inventors: Michael Lindars, Portland, OR (US); Robert Niemeyer, Tigard, OR (US)

(73) Assignee: ICONIC VENTURES, INC., Portland, OR (US)

( * ) Notice: Subject to any disclaimer, the term of this patent is extended or adjusted under 35 U.S.C. 154(b) by 0 days.

(21) Appl. No.: 16/380,948

(22) Filed: Apr. 10, 2019

(65) Prior Publication Data

US 2019/0232253 A1 Aug. 1, 2019

Related U.S. Application Data

(63) Continuation-in-part of application No. 15/950,083, filed on Apr. 10, 2018, now Pat. No. 10,413,685.

(Continued)

(51) Int. Cl.
*B01J 20/28* (2006.01)
*A61M 11/04* (2006.01)
(Continued)

(52) U.S. Cl.
CPC ......... *B01J 20/28085* (2013.01); *A24F 40/42* (2020.01); *A61M 11/041* (2013.01);
(Continued)

(58) Field of Classification Search
CPC ........................ B01J 20/28; B01J 20/28002; B01J 20/28004; B01J 20/28007; B01J 20/28009; B01J 20/28; B01J 20/28069; B01J 20/28071; B01J 20/28073; B01J 20/28076; B01J 20/28078; B01J 20/2808; B01J 20/28083; B01J 20/28085; B65D 25/02; B65D 2201/00; B65D 2581/34; A61M 15/00–085; A61M 11/041;
(Continued)

(56) References Cited

U.S. PATENT DOCUMENTS

| 4,913,169 A | 4/1990 | Templeton |
| 4,989,619 A | 2/1991 | Clearman et al. |

(Continued)

FOREIGN PATENT DOCUMENTS

| CA | 2931486 A1 | 5/2015 |
| WO | 2006/015148 A1 | 2/2006 |

(Continued)

OTHER PUBLICATIONS

International Search Report and Written Opinion dated May 16, 2019 for International Application No. PCT/US2019/016706.

(Continued)

*Primary Examiner* — Elliot S Ruddie
(74) *Attorney, Agent, or Firm* — Mackey Law Firm PLLC

(57) ABSTRACT

A device for storing oil or another vaporizable substance can include a porous body adapted to absorb a volume of liquid and to retain the volume of liquid for vaporization. A porous body can include a matrix of pores adapted to take up and retain oil by capillary action. A method of vaporizing oil can include storing the oil in a porous body and heating the porous body.

20 Claims, 7 Drawing Sheets

Related U.S. Application Data

(60) Provisional application No. 62/760,924, filed on Nov. 14, 2018, provisional application No. 62/756,362, filed on Nov. 6, 2018, provisional application No. 62/626,451, filed on Feb. 5, 2018, provisional application No. 62/483,868, filed on Apr. 10, 2017.

(51) Int. Cl.
  *B65D 25/02* (2006.01)
  *A24F 40/42* (2020.01)
  *A24F 40/10* (2020.01)

(52) U.S. Cl.
  CPC .............. *B65D 25/02* (2013.01); *A24F 40/10* (2020.01); *A61M 2205/8206* (2013.01); *B65D 2201/00* (2013.01); *B65D 2581/34* (2013.01)

(58) Field of Classification Search
  CPC .... A61M 11/042; A61M 11/04; A61M 11/07; A61M 2205/3368; A61M 2205/3372; A61M 2205/3375; A61M 2205/3653; A61M 2205/368; A61M 2205/50; A61M 2205/8206; A61M 16/1075–109; A61M 16/16; A61M 16/1045; A61K 9/007; A61K 9/0073; A61K 9/0078; A61K 47/44; A24F 47/00; A24F 47/002; A24F 47/004; A24F 47/008; A24F 42/00–90
  USPC ............ 128/202.21; 131/191, 193, 216, 217, 131/218, 225, 226, 260, 330, 309, 310, 131/329, 900, 901, 902, 903
  See application file for complete search history.

(56) References Cited

U.S. PATENT DOCUMENTS

| | | | |
|---|---|---|---|
| 5,137,034 | A | 8/1992 | Perfetti et al. |
| 5,840,246 | A | 11/1998 | Hammons et al. |
| D682,465 | S | 5/2013 | Yeom |
| D747,548 | S | 1/2016 | Mayor |
| 9,320,300 | B2 | 4/2016 | Hon |
| D760,952 | S | 7/2016 | Mayor |
| D787,114 | S | 5/2017 | Scott |
| D805,687 | S | 12/2017 | Perez et al. |
| 9,943,108 | B2 | 4/2018 | Lord |
| 9,986,760 | B2 | 6/2018 | Macko et al. |
| 10,004,682 | B2 | 6/2018 | Muzzio et al. |
| 10,034,990 | B2 | 7/2018 | Mccullough |
| D827,196 | S | 8/2018 | Sudlow |
| D827,920 | S | 9/2018 | Fornarelli |
| 2008/0112857 | A1 | 5/2008 | McKenzie-Jones et al. |
| 2011/0171077 | A1 | 7/2011 | McKenzie-Jones et al. |
| 2012/0093902 | A1 | 4/2012 | Artiga-Gonzalez et al. |
| 2013/0192623 | A1 | 8/2013 | Tucker et al. |
| 2013/0255702 | A1 | 10/2013 | Griffith, Jr. et al. |
| 2013/0319407 | A1 | 12/2013 | Liu |
| 2014/0069424 | A1 | 3/2014 | Poston et al. |
| 2014/0299137 | A1 | 10/2014 | Kieckbusch et al. |
| 2015/0136124 | A1 | 5/2015 | Aronie et al. |
| 2015/0136158 | A1* | 5/2015 | Stevens ................. H02J 7/0047 |
| | | | 131/329 |
| 2015/0208728 | A1* | 7/2015 | Lord ......................... A24F 7/00 |
| | | | 131/329 |
| 2015/0272216 | A1 | 10/2015 | Dai et al. |
| 2016/0228658 | A1* | 8/2016 | Minskoff .......... A61M 15/0033 |
| 2016/0295914 | A1 | 10/2016 | Jordil et al. |
| 2016/0360790 | A1 | 12/2016 | Calfee et al. |
| 2017/0156399 | A1 | 6/2017 | Freeman et al. |
| 2017/0215481 | A1 | 8/2017 | Li et al. |
| 2017/0224018 | A1 | 8/2017 | Li et al. |
| 2017/0231286 | A1 | 8/2017 | Borkovec et al. |
| 2017/0340018 | A1 | 11/2017 | Thorens |
| 2017/0360095 | A1 | 12/2017 | Batista |
| 2017/0367411 | A1 | 12/2017 | Duc |
| 2018/0014576 | A1 | 1/2018 | White |
| 2018/0020723 | A1* | 1/2018 | Davis ....................... H05B 3/44 |
| | | | 392/404 |
| 2018/0132534 | A1 | 5/2018 | Reevell |
| 2018/0162769 | A1* | 6/2018 | Peuchert .............. A61M 11/042 |
| 2018/0177231 | A1 | 6/2018 | Woodbine et al. |
| 2018/0177240 | A1* | 6/2018 | Duque ..................... H05B 3/06 |
| 2018/0206553 | A1 | 7/2018 | Reevell |
| 2018/0220710 | A1 | 8/2018 | Marks et al. |
| 2018/0221605 | A1 | 8/2018 | Marks et al. |
| 2018/0255834 | A1 | 9/2018 | Dillmann et al. |
| 2018/0255835 | A1 | 9/2018 | Crowe et al. |
| 2018/0289909 | A1 | 10/2018 | Lindars et al. |
| 2018/0295886 | A1 | 10/2018 | Freeman et al. |
| 2018/0333547 | A1 | 11/2018 | Freeman et al. |
| 2019/0029318 | A1 | 1/2019 | Schneider |
| 2019/0231992 | A1* | 8/2019 | Skoda .................. A61M 11/042 |

FOREIGN PATENT DOCUMENTS

| | | |
|---|---|---|
| WO | 2011146174 A2 | 2/2012 |
| WO | 2015107552 A1 | 7/2015 |
| WO | 2017001352 A3 | 2/2017 |
| WO | 2018037245 A1 | 3/2018 |

OTHER PUBLICATIONS

International Search Report and Written Opinion dated Jan. 17, 2019 for International Application No. PCT/US2018/026976.
Lucky Edibles—Cannabis Infused Flavored Mints, accessed Nov. 20, 2018, www.luckyedibles.com.
Statement of Trademark Registration of a Reporting Entity, Jul. 28, 2014, ID No. 20141459355, Colorado Secretary of State, USA.
Statement of Trademark Registration of a Reporting Entity, Sep. 15, 2016, ID No. 20161623092, Colorado Secretary of State, USA.
Statement of Trademark Registration of a Reporting Entity, Oct. 31, 2016, ID No. 20161743535, Colorado Secretary of State, USA.
Statement of Trademark Registration of a Reporting Entity, Oct. 31, 2016, ID No. 20161743695, Colorado Secretary of State, USA.
Vape Pen Mesh Coil, accessed Oct. 2, 2018, pp. 1-12, www.smoktech.com.
Filtros Limited, website printouts from https://filtrosltd.com/material-product-faq, 11 pages, accessed Nov. 19, 2019.
International Search Report and Written Opinion dated Jul. 11, 2019 for International Application No. PCT/US2019/026857.
EPO Application No. 19747145.1, Extended European Search Report dated Nov. 2, 2021.
Anonymous: "Sintering—Wikipedia" Apr. 9, 2018, pp. 1-17, XP055880709, Retrieved from the Internet: URL:https://en.wikipedia.org/w/index.php?title=Sintering&oldid=835548268 [retrieved on Jan. 18, 2022].
Anonymous: "Porous glass—Wikipedia" Jan. 5, 2018, pp. 1-5, XP055880714, Retrieved from internet: URL: https//en.wikipedia.org/w/index.php?title+Porous_glass&oldid=818841798 [retrieved on Jan. 18, 2022].
EPO Application No. 19784422.8, Extended European Search Report dated Jan. 27, 2022.

* cited by examiner

VAPORIZABLE SUBSTANCE STORAGE DEVICE

CROSS REFERENCE TO RELATED APPLICATIONS

This application claims the benefit of U.S. Provisional Patent Application No. 62/756,362 filed Nov. 6, 2018 and U.S. Provisional Patent Application No. 62/760,924 filed Nov. 14, 2018, and is a continuation-in-part of U.S. patent application Ser. No. 15/950,083 filed Apr. 10, 2018, which claims the benefit of U.S. Provisional Patent Application No. 62/483,868 filed Apr. 10, 2017 and U.S. Provisional Patent Application No. 62/626,451 filed Feb. 5, 2018, the entire contents of which are hereby incorporated by reference into this disclosure.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

Field of the Invention

The present disclosure relates generally to storage devices for vaporizable substances and more specifically relates to devices for storing vaporizable substances and supporting vaporization during heating.

Description of the Related Art

A vaporizer or other heating device can be used to convert oil or another substance, such as a substance that contains medication or other compounds, to a vapor or mist for inhalation by a user. Oils can be used to prevent damage to medications that may be sensitive to solvents or propellants used in applications like asthma inhalers, or for medications or compounds that cannot be dissolved in water. In some cases, a vaporizable substance can exist in the form of an oil, whether that be naturally, as a result of a manufacturing or production process, or otherwise. For example, extracts from the cannabis plant can take the form of an oil or oil-like substance that can be heated via an oral vaporizer or other heating device for inhalation by a user. However, cannabis extracts can take numerous different forms having differing physical characteristics, which can include differences in viscosity, brittleness, tackiness or stickiness, or density, among other attributes. Moreover, in some cases, cannabis extracts can be corrosive to metal, plastic, or other materials, such as materials used to store the extracts or to manufacture the various components in a vaporizer or other heating device. The foregoing characteristics can in at least some cases make cannabis extracts difficult or undesirable to work with or use, including by way of difficulties in storage or transportation of the extracts, such as prior to vaporization. For instance, the variations among forms can present problems pertaining to the use of different forms in or with a single heating device and the physical characteristics can make for difficult or tedious cleaning of any heating device components with which the extracts come in contact. As another example, the corrosiveness or acidity of the extracts can degrade containers, seals and other components, which can tend to cause leakage of extracts from storage containers, heating devices or components thereof, such as oil reservoirs or cartridges.

As another example, at least some conventional vaporizers include wicking devices for transferring oil from a storage reservoir to an area for physical or thermal contact with a heating element. However, such wicking devices can result in leaking of oil from the vaporizer, such as onto a user's hand or clothing. Excessive wicking can foul a heating element or other components, such as by providing too much fluid to heat to the vaporization point. Excessive wicking may also clog air channels within the device or leave oil exposed to air, which may result in malfunctions or, e.g., allow volatile medication dissolved in the oil to evaporate. In some cases, such evaporation may cause the oil's viscosity to change to a point that prevents the oil from being re-liquefied or vaporized within the device. Excessive wicking and clogging may lead to the loss of some or all of the oil contained in a vaporizer, or even render the vaporizer inoperable such that repair or replacement may be needed. As further examples, in some cases, the oil used in the vaporizer can be corrosive (e.g., having a PH between 8 and 11.5) and may come into contact with metal or other parts within the device, which can result in a metallic or other taste that may be undesirable to some users or damage to one or more components. Additionally, conventional heating devices may lack a manner of recycling or trapping condensed oil within the device for preventing waste or leaking of the oil.

Accordingly, a need exists in the art for an improved manner of holding oils or other vaporizable substances prior to and during heating or vaporization. The disclosures and teachings herein are directed to devices, systems and methods for improved vaporizable substance storage devices.

BRIEF SUMMARY OF THE INVENTION

A device for storing a vaporizable substance can include a porous body having a top, a bottom and an exterior surface. The body can be adapted to absorb a volume of liquid through openings in at least a portion of the exterior surface and to retain the volume of liquid within internal pores until at least a portion of the volume of liquid can be vaporized. A body can be adapted to retain its shape and pore volume independently of contact with water. A device can be adapted to absorb cannabis oil by capillary action. A device can be adapted to retain a volume of cannabis oil within pores interior of the exterior surface of the body. A device can be adapted to retain a maximum weight of cannabis oil, such as 0.05 gram, or more or less.

Openings in a body can be at least substantially uniformly disposed about an entire exterior surface of the body. Internal pores of a body can be at least substantially uniformly disposed throughout the entire body. Internal pores of a body can be of an at least substantially uniform pore size. A body can have a pore size of 0.5 micron, or more or less. For example, a body can have a pore size of 15 microns, which can be a maximum pore size, with a 0.5 micron particle retention. As another example, a body can be configured to retain (or at least partially prevent passage of) particles having a size in the range of 0.5 micron to 50 microns or so. At least a portion of a body can be a solid. At least one of a body's shape and pore volume can be fixed.

A body can be adapted to at least partially resist melting and/or burning at an ambient temperature of at least 450° F., or more or less. A body can be adapted to retain a volume of liquid by capillary action. An exterior surface of a body can include a radially exterior surface, which can have a plurality of quadrilateral sides. A body can include one or more partial or thru holes. At least a portion of an exterior surface of a body can be concave or convex. A volume of oil can be stored within at least a portion of a plurality of internal pores. A total exterior surface of a body can bound a total body volume. A total body volume can be less than or equal to 0.1 cubic inch, or more.

A device for storing a vaporizable substance can include a porous body having a top, a bottom and one or more sides. A porous body can include a first plurality of pores that comprise openings in an exterior surface of the body and a second plurality of pores disposed wholly or partially within the body. At least a portion of a second or other plurality of pores can be disposed in fluid communication with at least one of a first or other plurality of pores. A porous body can be adapted to take in a volume of oil through openings by capillary action and to retain the volume of oil within one or more of a plurality of pores. A body can be adapted to store or hold oil for vaporization by heating.

A porous body can be adapted to retain its shape and pore volume independently of contact with water or other substances or conditions, including chemicals or temperature. A porous body can be adapted to at least partially resist egress or leakage of oil through exterior openings absent heating or vaporization of the oil. A porous body can be adapted to release or allow release of vaporized oil. A porous body can be adapted to take in and retain liquid cannabis oil. A porous body can be adapted to be heated to a temperature equal to or greater than a vaporization temperature of the cannabis oil. At least one of one or more sides of a porous body can be quadrilateral, or another shape.

A method of storing a vaporizable substance can include disposing one or more devices of the present disclosure in contact with a first volume of oil and removing the device(s) from contact with a remainder of the first volume of oil. Removal can take place after a time period or, for example, after a second or other volume of oil is disposed within a device. A second or other volume of oil can be a portion of a first volume of oil. A method can include storing one or more devices of the disclosure. A method can include at least one of heating one or more devices, heating oil, removing oil from a surface or other portion of a device and a combination thereof. A method can include packaging or otherwise preparing a device of the present disclosure for heating or vaporization of oil within the device.

DETAILED DESCRIPTION

Figure 1:
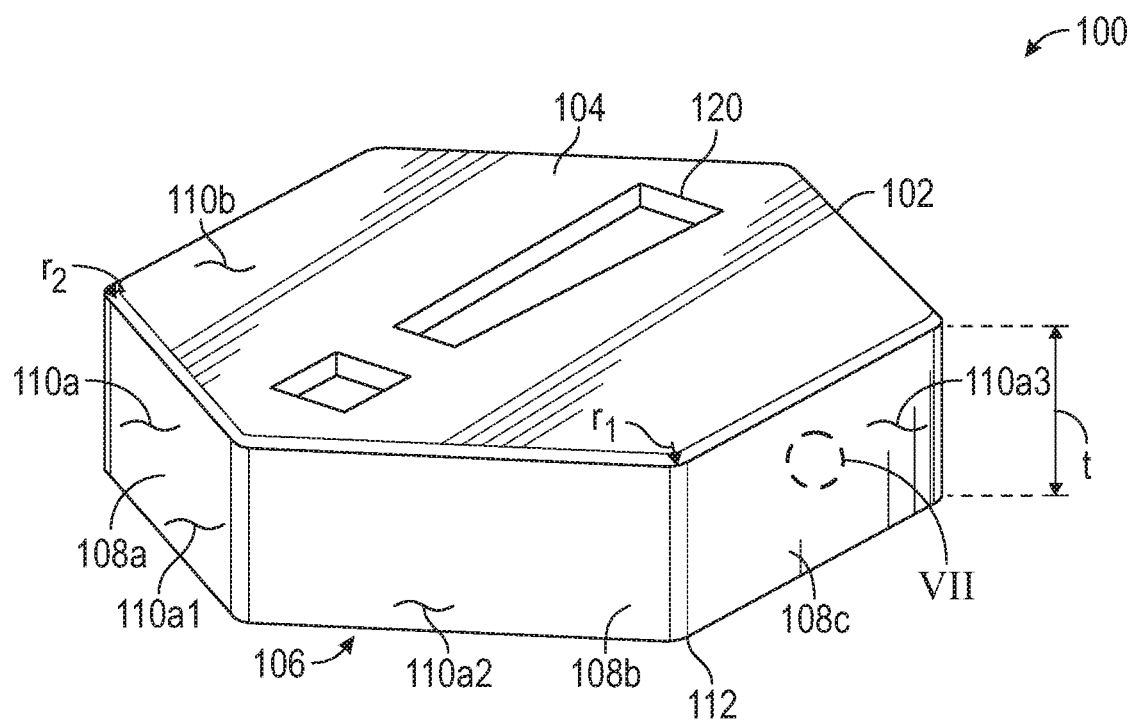
FIG. 1 is a perspective view of one of many embodiments of a vaporizable substance storage device according to the disclosure.

The Figures described above and the written description of specific structures and functions below are not presented to limit the scope of what Applicants have invented or the scope of the appended claims. Rather, the Figures and written description are provided to teach any person skilled in the art to make and use the invention(s) for which patent protection is sought. Those skilled in the art will appreciate that not all features of a commercial embodiment of the disclosure are described or shown for the sake of clarity and understanding. Persons of skill in this art will appreciate that the development of an actual commercial embodiment incorporating aspects of the present disclosure can require numerous implementation-specific decisions to achieve the developer's ultimate goal for the commercial embodiment(s). Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of skill in the art having the benefits of this disclosure.

The embodiment(s) disclosed and taught herein are susceptible to numerous and various modifications and alternative forms. The use of a singular term, such as, but not limited to, "a," is not intended as limiting of the number of items. The use of relational terms, such as, but not limited to, "top," "bottom," "front," "rear," "left," "right," "upper," "lower," "down," "up," "side," "first," "second," "inlet," "outlet" and the like are used in the written description for clarity in specific reference to the Figures and are not intended to limit the scope of the disclosure or the appended claims unless otherwise indicated. The terms "couple," "coupled," "coupling," "coupler," and like terms are used broadly herein and can include any method or device for securing, binding, bonding, fastening, attaching, joining, inserting therein, forming thereon or therein, communicating, or otherwise associating, for example, mechanically, magnetically, electrically, chemically, operably, directly or indirectly with intermediate elements, one or more pieces of members together and can further include without limitation integrally forming one member with another in a unity fashion. The coupling can occur in any direction, including rotationally. The terms "include" and "such as" are illustrative and not limitative, and the word "can" means "can, but need not" unless otherwise indicated. The term "end" can, but need not, be or include a terminal end unless otherwise indicated. Notwithstanding any other language in the present disclosure, the embodiment(s) shown in the drawings are examples presented for purposes of illustration and explanation and are not the only embodiments of the subject(s) hereof.

Applicants have created devices, systems and methods for containing, storing, transporting and/or releasing upon vaporization one or more vaporizable substances, including oils such as cannabis oil (e.g., cannabidiol (CBD) oil and derivatives thereof, tetrahydrocannabinol (THC) oil and derivatives thereof) and others. Applicants have created devices for containing, storing, transporting and/or releasing upon vaporization one or more oils and at least partially minimizing or eliminating one or more difficulties conventionally associated with using or working with such oils or conventional containers for such oils, including, but not limited to, difficulties relating to material handling, cleanup, viscosities, differences in form or consistency among oils and related substances of the same or similar natures, acidity, corrosiveness, stickiness, brittleness, messiness and tendencies to clog or damage equipment such as vaporizers or other heating devices. Applicants have created devices, systems and methods for containing, storing, transporting and/or releasing upon vaporization one or more oils, which can include doing so independently from or in the absence of a conventional fluid reservoir or other container comprised of fluid-impermeable or waterproof walls or other barriers (e.g., bottoms, tops, etc.) made from materials such as plastic, aluminum or glass. Applicants have created devices, systems and methods for holding oil, which can include devices, systems and methods for storing, transporting, conveying or otherwise supporting oil prior to, during and/or subsequently to heating of oil for vaporization and human inhalation. Applicants have created devices, systems and methods for providing a convenient and clean way for users to transport or store oil for use in a vaporizer. The devices, systems and methods of the present disclosure can be adapted for use with numerous different types of oil, separately or in combination, which can include, but is not limited to, cannabis oils or extracts such as those mentioned above and/or other oils, such as oils having medication or another consumable substance(s) therein or otherwise associated therewith. Such oils can, but need not, include or be combined with one or more other substances, such as medicine or a mixture of substances including a carrier fluid or solvent, whether miscible or otherwise. Additional functions and aspects of the devices, systems and methods of the present disclosure are described in further detail below with reference to the Figures.

Figure 2:
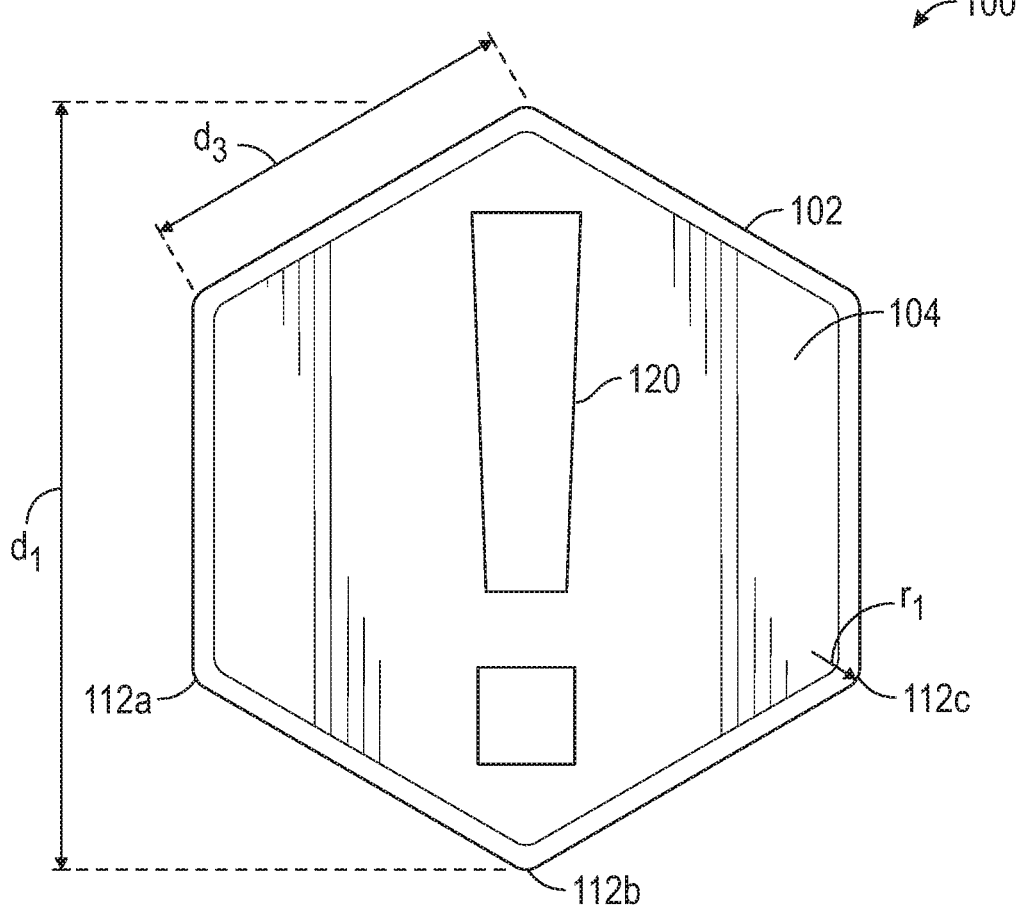
FIG. 2 is a front view of the device of FIG. 1.
Figure 3:
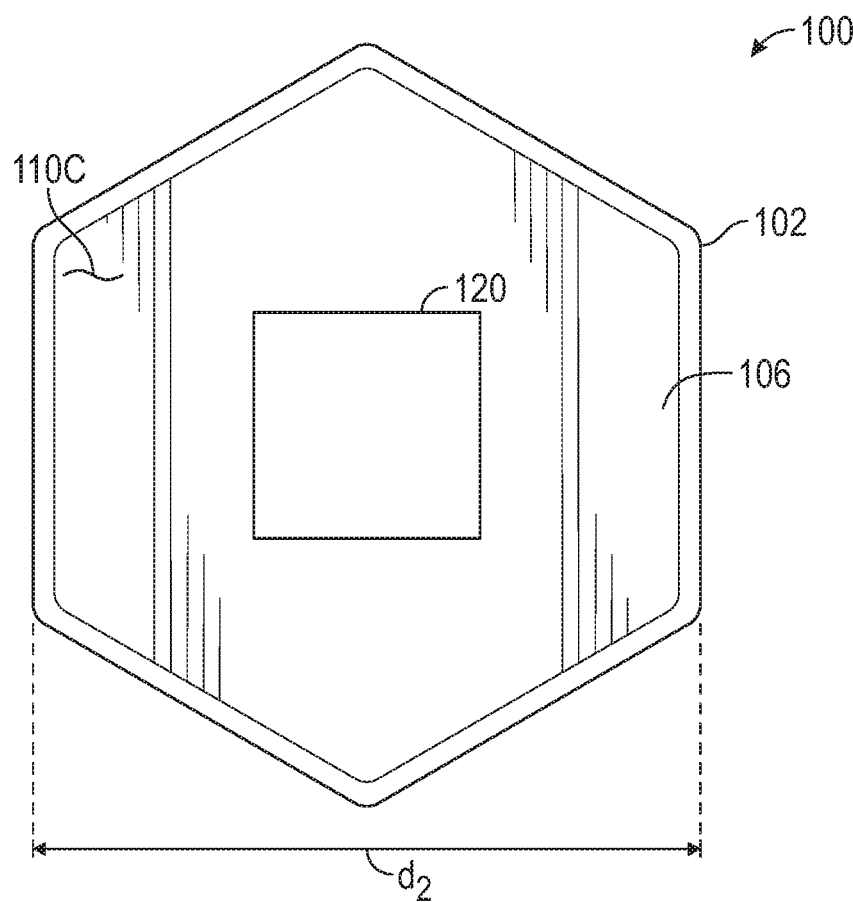
FIG. 3 is a rear view of the device of FIG. 1.
Figure 4:
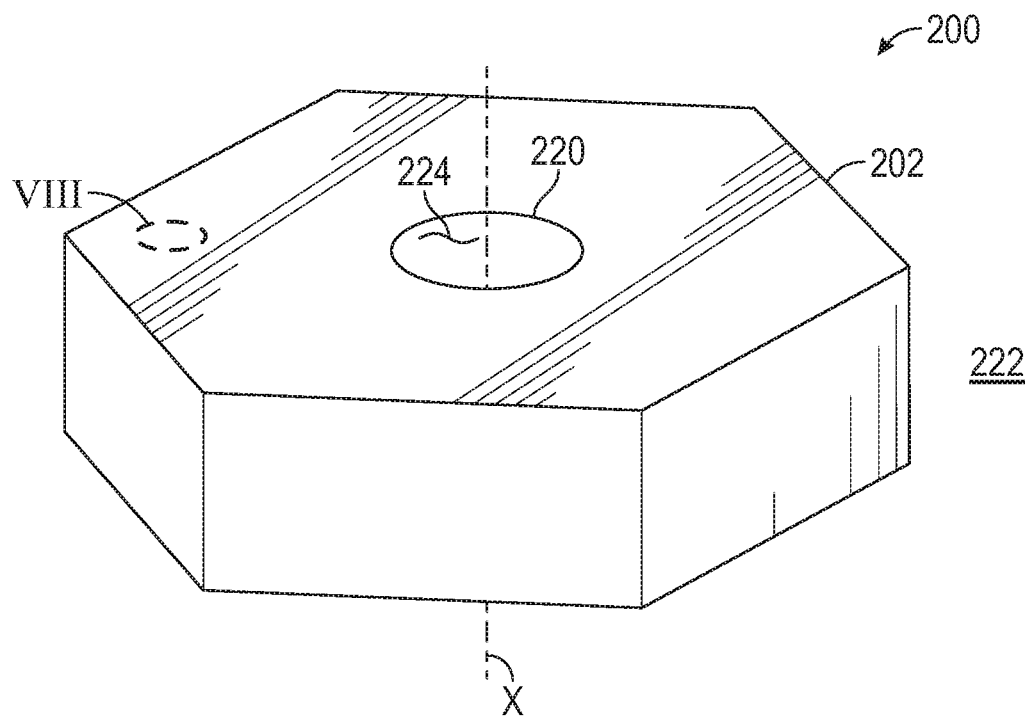
FIG. 4 is a perspective view of another of many embodiments of a vaporizable substance storage device according to the disclosure.
Figure 5:
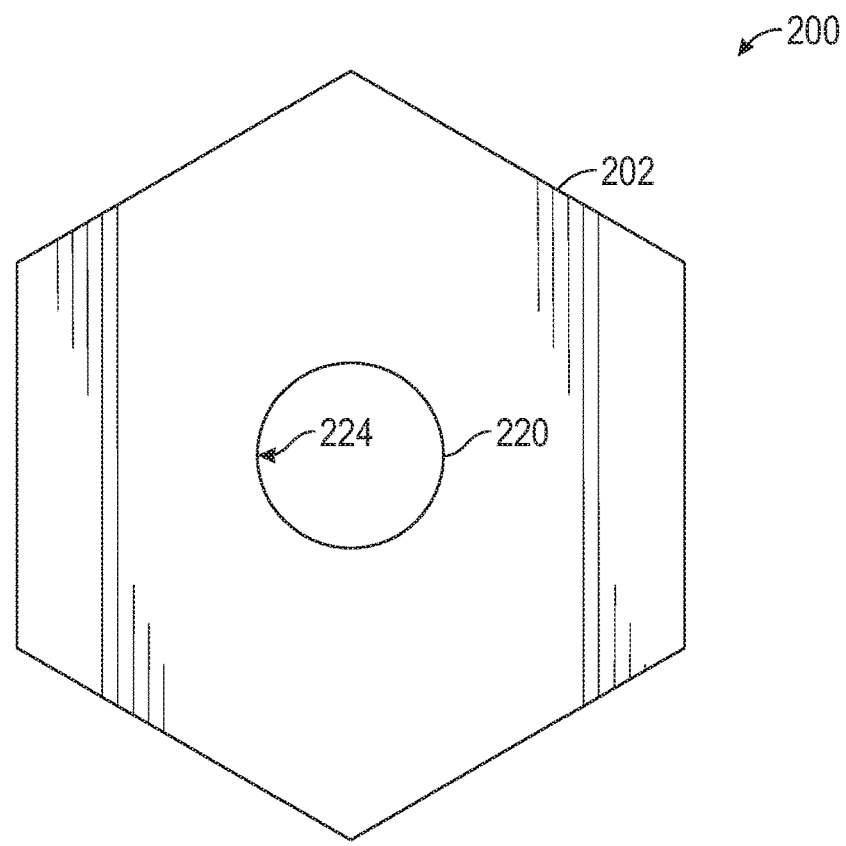
FIG. 5 is a front view of the device of FIG. 4.
Figure 6:
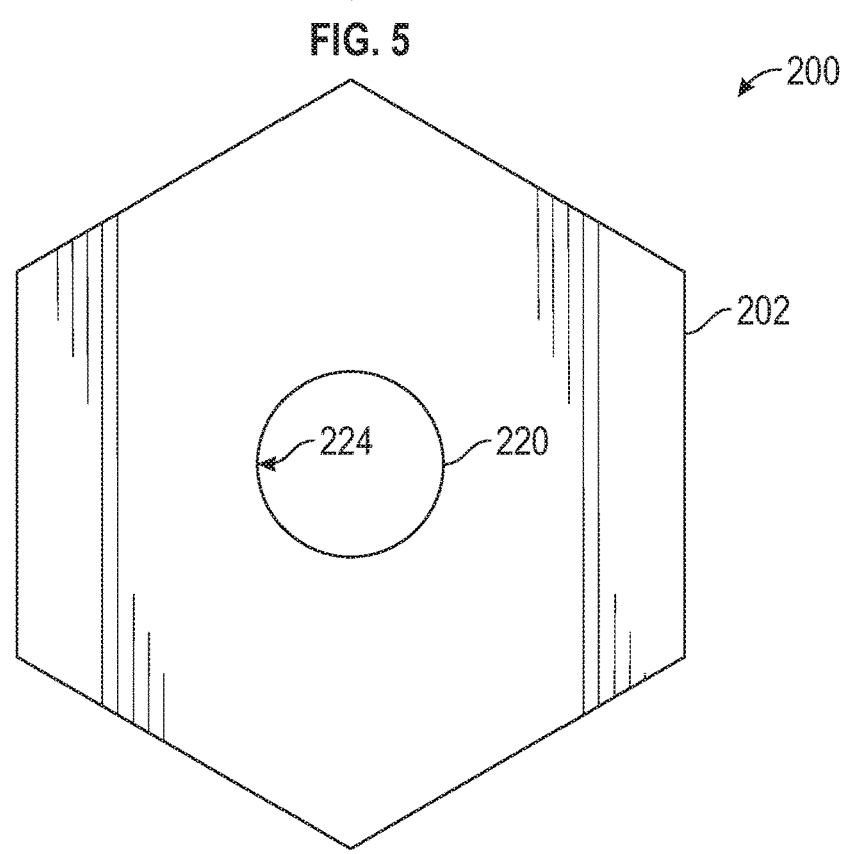
FIG. 6 is a rear view of the device of FIG. 4.
Figure 7:
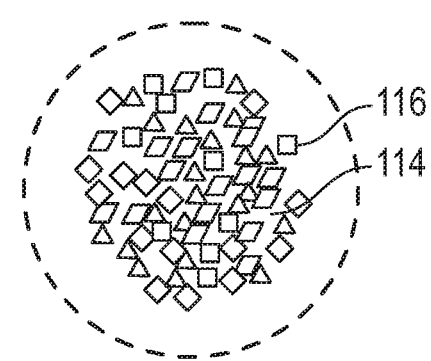
FIG. 7 is a schematic detail view of one of many embodiments of a pore structure according to the disclosure.
Figure 8:
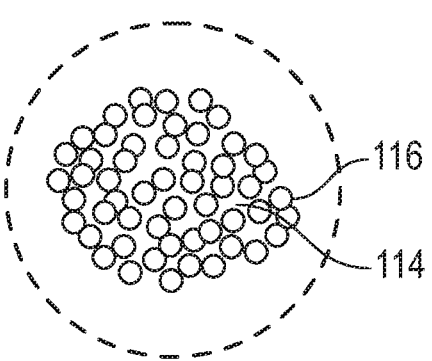
FIG. 8 is a schematic detail view of another of many embodiments of a pore structure according to the disclosure.
Figure 9:
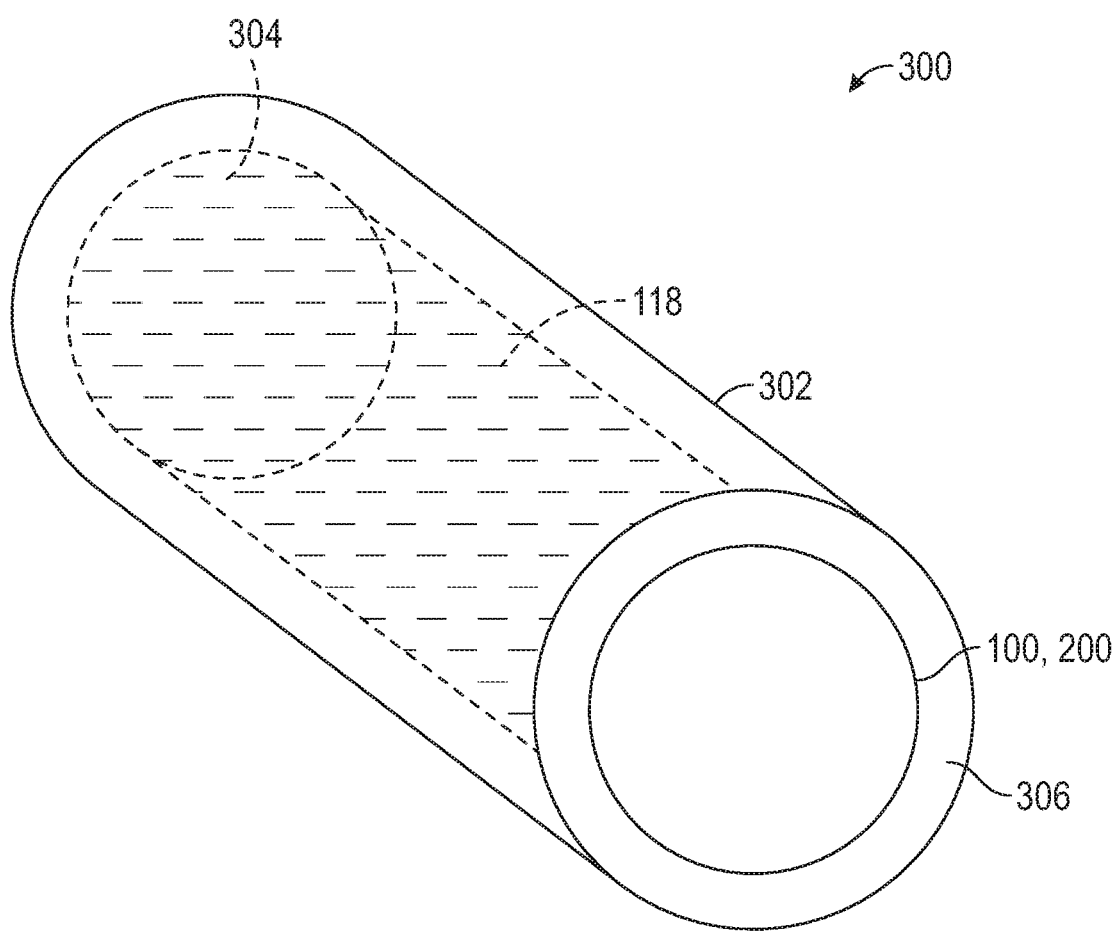
FIG. 9 is a perspective view of one of many embodiments of a cartridge according to the disclosure.
Figure 10:
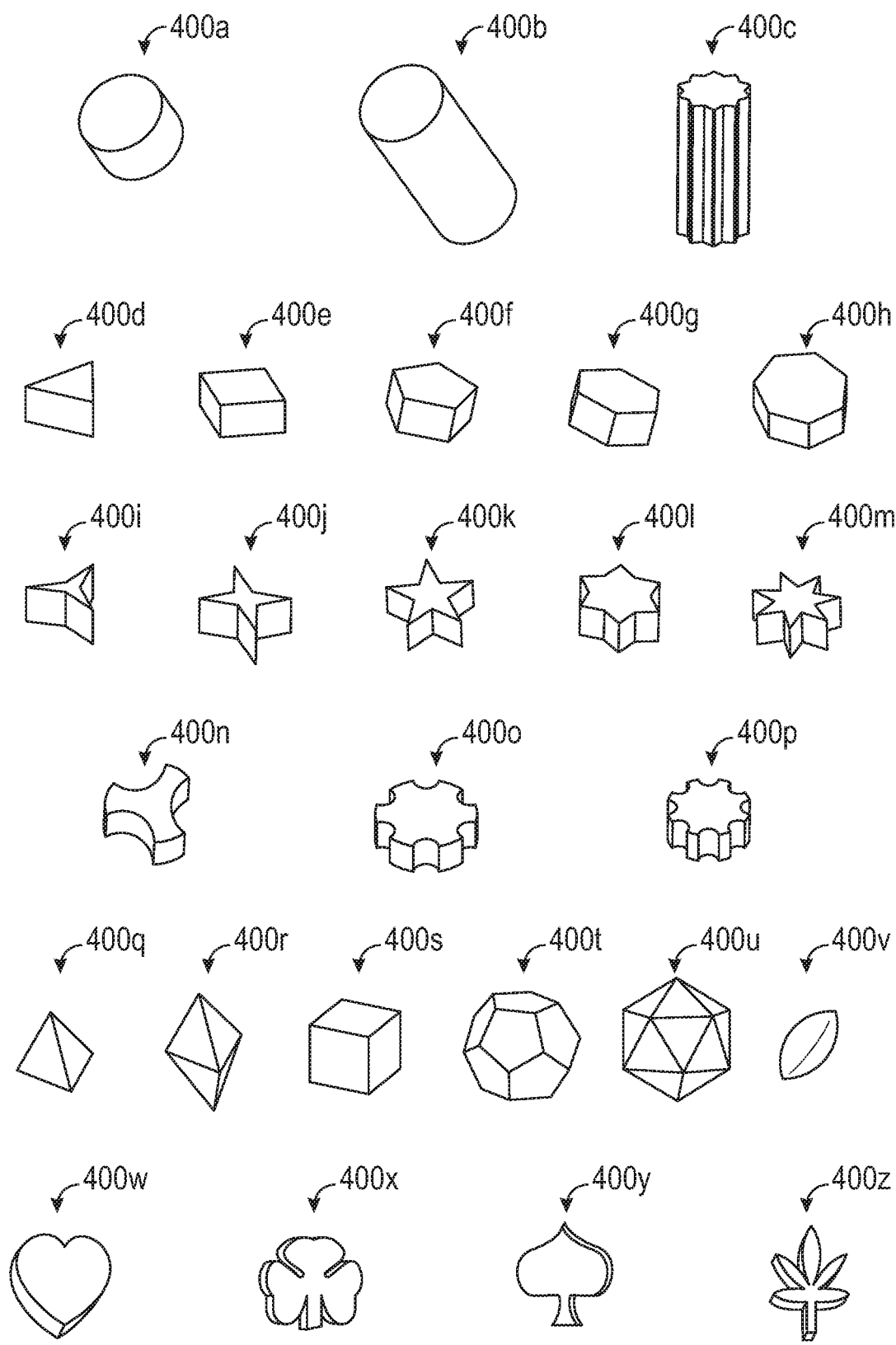
FIG. 10 includes perspective views of other of many embodiments of a vaporizable substance storage device according to the disclosure.
Figure 11:
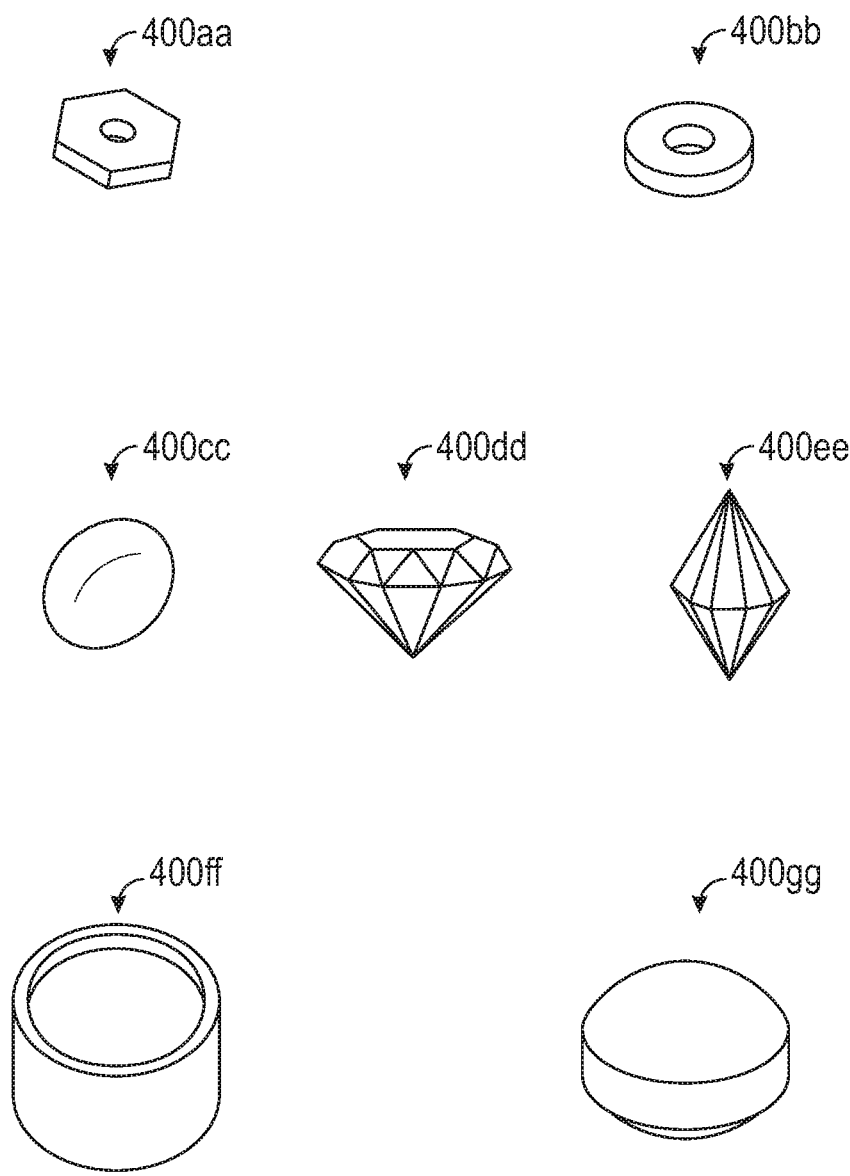
FIG. 11 includes perspective views of yet other of many embodiments of a vaporizable substance storage device according to the disclosure.
Figure 12:
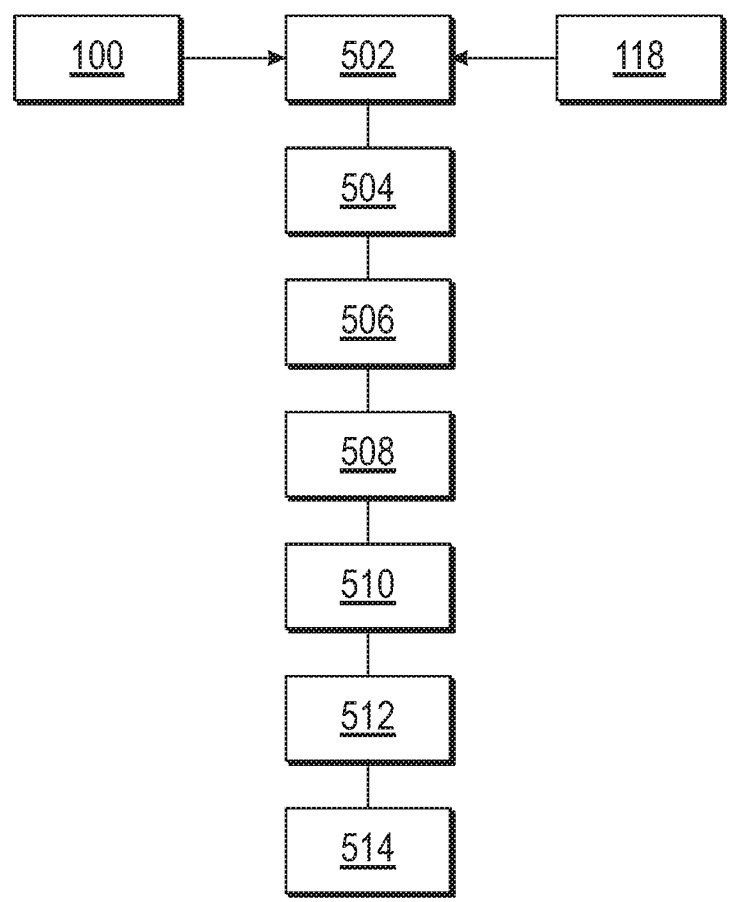
FIG. 12 is a flow chart schematically illustrating one of many embodiments of a method according to the disclosure.

FIG. 1 is a perspective view of one of many embodiments of a vaporizable substance storage device according to the disclosure. FIG. 2 is a front view of the device of FIG. 1. FIG. 3 is a rear view of the device of FIG. 1. FIG. 4 is a perspective view of another of many embodiments of a vaporizable substance storage device according to the disclosure. FIG. 5 is a front view of the device of FIG. 4. FIG. 6 is a rear view of the device of FIG. 4. FIG. 7 is a schematic detail view of one of many embodiments of a pore structure according to the disclosure. FIG. 8 is a schematic detail view of another of many embodiments of a pore structure according to the disclosure. FIG. 9 is a perspective view of one of many embodiments of a cartridge according to the disclosure. FIG. 10 includes perspective views of other of many embodiments of a vaporizable substance storage device according to the disclosure. FIG. 11 includes perspective views of yet other of many embodiments of a vaporizable substance storage device according to the disclosure. FIG. 12 is a flow chart schematically illustrating one of many embodiments of a method according to the disclosure. FIGS. 1-12 are described in conjunction with one another.

In at least one embodiment, a system or device 100 for storing one or more vaporizable substances can be or include a body 102 for holding one or more oils or other vaporizable substances, separately or in combination with one another and/or with one or more nonvaporizable substances, in whole or in part. As shown in the exemplary embodiment of FIG. 1, which is but one embodiment of many, device 100 can be or include a unitary body 102; however, this need not be the case and, in at least one embodiment, device 100 can include one or more bodies 102 coupled to one another and/or to one or more other device components, such as, for example, a housing, frame, coupler, or other structure for supporting one or more bodies 102 or a portion thereof (see, e.g., FIG. 9 (further described below)). In at least one embodiment, body 102 can have a top 104, a bottom 106 and one or more sides 108a, 108b, 108c . . . 108n (collectively, side(s) 108), such as radially exterior sides (about, e.g., a central longitudinal axis X or other axis (see, e.g., FIG. 4)) or other sides, and an exterior surface 110. Top 104, bottom 106 and sides 108 can include corresponding top, bottom and side surfaces that can collectively form or otherwise constitute at least a portion of exterior surface 110. For instance, one or more sides 108 can form or otherwise constitute at least a portion of exterior surface 110, such as a radially exterior surface 110a that, collectively with top surface 110b and bottom surface 110c, comprise exterior surface 110. Similarly, radially exterior surface 110a can, in at least one embodiment, comprise a plurality of surfaces 110a1, 110a2, 110a3 . . . 110an, which can include surfaces of one or more sides 108 and/or other surfaces, such as intervening surfaces disposed between or otherwise relative to adjacent or successive sides 108. Alternatively, or collectively, radially exterior surface 110a can be at least partially endless or free of any vertices 112a, 112b, 112c . . . 112n (collectively, vertices 112), such as in an embodiment having a circular or at least partially arcuate cross-section (see, e.g., FIGS. 10-11). One or more vertices 112 (if present), which can, but need not include, all vertices, can be sharp or cornered (see, e.g., FIG. 4) or can be contoured, curved, such as by having one or more radii (see, e.g., FIG. 1), chamfered, or otherwise shaped, separately or in combination, in whole or in part.

Device 100 or a portion thereof, such as body 102, can include one or more dimensions, which can be or include any dimension(s) according to an implementation of the disclosure, such as exterior dimensions, interior dimensions, cross-sectional dimensions, or other dimensions, which can comprise dimensions referenced relative to a position or orientation (e.g., heights, widths, lengths), directionally (e.g., along an x, y, or z axis), arbitrarily, or otherwise. For example, device 100 can include a major dimension d1, a minor dimension d2, a thickness t and/or one or more other dimensions, such as a segment or side dimension d3, or one or more radii, such as radius r1 (of vertex 112) and radius r2 (of rounded edge). In at least one embodiment, major dimension d1 or another dimension can be or include a diameter (see, e.g., FIGS. 9-10). Similarly, device 100 or a portion thereof, such as body 102, can include one or more areas, such as one or more internal, external or other surface areas, and once or more volumes, such as one or more internal, total or other volumes. For example, top 104, bottom 106 and sides 108 can each have a surface area, such as an exterior surface area, which can collectively comprise a total surface area of device 100. As another example, top 104, bottom 106 and sides 108 can define, enclose or otherwise bound a volume, which can include a total volume, of device 100. As yet another example, device 100 or a portion thereof, such as body 102, can include one or more pores (further described below), each of which can have an internal surface area and a volume and all of which can, in at least one embodiment, collectively constitute a total internal surface area and total internal volume of device 100 or body 102, which can be or include any area or volume according to an implementation of the disclosure.

Device 100 can be adapted to hold oil in at least a portion thereof. In at least one embodiment, device 100 or a portion thereof, such as body 102 or a portion of body 102, can be partially or wholly porous and can include one or more pores 114 for holding oil, such as openings, voids, or spaces disposed between or among material units 116, such as particles, beads, molecules, or other portions of a component material(s) from which body 102 can be made (see, e.g., FIGS. 7-8). Pores 114 can be any size or shape according to an implementation of the disclosure and can be uniform in size and/or shape or nonuniform in size and/or shape, separately or in combination, in whole or in part. In at least one embodiment, pores 114 can be sized and shaped for receiving oil and for retaining at least a portion of oil therein, which can include receiving, retaining or otherwise holding oil by capillary action. Accordingly, pores 114 can be sized and shaped for cooperating with one or more oils by capillary action and such sizes and shapes can vary among implementations of the disclosure based on one or more factors, such as the type of oil (or other vaporizable substance) for which or with which a physical embodiment of device 100 will be used. For instance, variables such as viscosity and molecular size or other physical or environmental characteristics can factor into a determination of an appropriate or desired shape(s) and/or size(s) for the pores 114 of a given implementation of device 100, including with regard to which size(s) and/or shape(s) of pores 114 accomplish relevant goals for such implementation of device 100, such as by way of taking up and/or retaining a volume of oil by capillary action (whether separately or in combination with other forces or mechanisms). In at least one embodiment, device 100 can include a plurality or pores in fluid communication with its exterior surface and adapted for absorbing or taking in cannabis oil by capillary action when the device is in contact with cannabis oil and the oil is within the temperature range of 150-250 degrees Fahrenheit.

In at least one embodiment, the size(s) and/or shape(s) of pores 114 can at least partially depend on or be controlled by the manner in which device 100 or body 102 is produced, which can include the production process(es) and the material(s) from which device 100 or body 102 is made. For example, in at least one embodiment, device 100 or body 102 can be produced by way of a molding process, which can include compressing one or more materials in a mold comprising one or more forms or openings sized and shaped to result in a device 100 or body 102 of a size and shape according to an implementation of the disclosure, which can be or include any size or shape, whether expressly disclosed herein or otherwise, separately or in combination, in whole or in part. For instance, in at least one embodiment, one or more component materials in a powder, granular, or similar form can be combined with a binding material, such as a glue, adhesive, or other substance for combining, and/or with a proppant, such as a material for making pores or other openings, and such a material or combination of materials can be molded or otherwise formed into device 100 or body 102, which can, but need not, include one or more steps for supporting such a molding process, such as heating, cooling, drying, hardening or chemical treating. In at least one embodiment, a component material, such as alumina or another material described herein, can be combined with a binding agent or other joining material and a proppant and formed into a device 100 or body 102 with pores 114 shaped and sized according to the shape and size of the proppant. In such an embodiment, which is but one of many, a proppant can have a lower melting point, boiling point, vaporization temperature, or burning temperature then a component material and/or binding agent, and the proppant can be removed following formation of a device 100 or body 102 of a desired shape and size by heating the device to a temperature that is greater than a melting point, boiling point, vaporization temperature, or burning temperature of the proppant and less than a melting point, boiling point, vaporization temperature, or burning temperature of the component material and/or binding agent. In this manner, or one or more other manners for removing a proppant from a device or body of the present disclosure, the proppant can be removed during or following production (or partial production) of a device 100 or body 102 thus leaving pores 114 within all or a portion of device 100 or body 102 in place of the proppant material.

Example component materials for device 100 or body 102 include porous ceramic, sintered metal, alumina (aka aluminum oxide), silicon carbide, passivated stainless steel, phosphor bronze, brass, ceramically bonded alumina, thermally fused alumina, fused silicon carbide, fused metallic beads, fibers (e.g., glass) and other materials of sufficient characteristics for forming pores configured to hold oil, separately or in combination with one another and/or one or more other materials disclosed herein, in whole or in part. Example binding agents for binding or coupling units of one or more component materials together include quartz glass, wax, polyethylene, glass powder, silicon dioxide (aka silica), or cotton-based material (e.g., cotton fibers that can decompose to form glass particles). Example proppants for forming one or more pores include sand, glass, salt, plastic, and polymers. However, other materials can also be used to form device 100 or body 102, whether separately or in combination with one or more of the exemplary materials described above or elsewhere herein and can, in at least one embodiment, include any material(s) capable of forming a porous body according to the disclosure, such as device 100 or body 102, whether now known or future developed. In at least one embodiment, device 100 can be or include a porous body 102 that can be or become relatively low in density and/or low in mass, which can help minimize an amount of energy sufficient to increase the temperature of oil coupled to device 100 to or above its vaporization point. In at least one embodiment, device 100 can be or include a porous body 102 comprising aluminum oxide coupled with quartz glass or another bonding material or agent. As will be understood by one of ordinary skill having the benefits of the present disclosure, embodiments of the disclosure can be configured for use with one or more types of oil, which can have differing vaporization temperatures, and the material and/or composition of device 100 or a portion thereof (e.g., body 102 or a portion thereof) can be chosen to facilitate flow, storage and/or vaporization of oils of different types as needed or desired for a physical embodiment or implementation of device 100. Factors relevant to such considerations can include, but are not limited to, pore size, capillary action characteristics, flow rate, density, material type, bonding agent type, proppant type, temperature, heat characteristics, chemical characteristics, pressure, compression rate and the like. The material(s) and pore size(s) of a device 100 can vary according to an implementation of the disclosure. For example, a device 100 can be adapted to absorb or otherwise store substances of different viscosities, densities, purities, or other attributes and can be or include one or more bodies 102 having a pore size(s) or material make up(s) optimized for cooperating with an oil(s) or other substance(s) at hand.

Example pore sizes for device 100 or body 102 include 30-90 microns or another pore size according to a physical embodiment or implementation of the disclosure, which can be any pore size, including pore sizes less than or greater than 30-90 microns, depending on oil type or other factors as mentioned elsewhere in this disclosure. In at least one embodiment, device 100 can include one or more pores 114 having a pore size and/or particle retention that is between about 0.5 microns and about 100 microns (inclusive). However, this need not be the case and, in at least one embodiment, device 100 can include one or more pores 114 having a dimension smaller than about 0.5 microns or larger than about 100 microns. Advantageously, in at least one embodiment of device 100 for use with cannabis oil, device 100 can include pores 114 having a pore size, such as an average or maximum pore size, of 15 microns or about 15 microns with a particle retention or maximum particle passage size of 0.5 micron or about 0.5 micron. As another example, a body can be configured to retain (or at least partially prevent passage of) particles having a size in the range of 0.5 micron to 50 microns or so. Pores 114 can, but need not, be of similar or the same shape and size and can, but need not, be of consistent dimension, which can depend on, for example, the type of material or method of manufacture. In at least one embodiment, device 100 can comprise numerous pores having similar, but not necessarily uniform characteristics, such as sizes and shapes that can differ from pore to pore. Nonetheless, such an embodiment of device 100 can be said to have a pore size, such as a mean or average pore size, maximum pore size, or minimum pore size, notwithstanding that one or more pores 114 can, in at least one embodiment, have more than one dimension, such as an irregularly or otherwise shaped pore having a major dimension, a minor dimension and/or one or more other dimensions.

In at least one embodiment, device 100 can be configured to absorb, take in or otherwise receive oil 118 (see, e.g., FIG. 9) or another substance(s), separately or in combination, which can include one or more vaporizable and/or non-vaporizable substances, including one or more solids disposed in or mixed with one or more oils, and can be configured to retain or otherwise hold at least a portion thereof in one or more pores 114. As mentioned elsewhere herein, device 100 can absorb and/or retain oil by way of capillary action; however, this need not be the case and other manners for holding oil exist. For example, in at least one embodiment, oil 118 can be relatively viscous and sticky when at a temperature within a normal range of ambient interior or exterior air temperatures (e.g., about 60-100° F. (about 15.5-37.8° C.)) and such viscosity and/or stickiness can decrease upon such oil 118 being heated. In such an embodiment, which is but one of many, pores 114 of device 100 can be shaped and sized such that oil 118 flows into or otherwise enters device 100 absent capillary action when oil 118 is at or above a corresponding temperature and/or remains within one or more pores 114 absent capillary action (e.g., by sticking thereto or otherwise becoming lodged therein) when oil 118 is at or below another corresponding temperature, such as a cooler temperature. Advantageously, however, in at least one embodiment, device 100 or a portion thereof, such as one or more bodies 102, can include one or more pores 114 shaped and sized for taking in and retaining vaporizable oil (e.g., cannabis oil) by capillary action.

In at least one embodiment, device 100 can absorb, take in or otherwise receive oil 118 and can retain or otherwise hold at least a portion thereof in pores 114 for supporting vaporization of oil 118 (or another transformation into a form or forms that can be inhaled). For example, device 100 can hold or store oil 118 until at least a portion of device 100 and/or the oil 118 contained therein is heated to a boiling point or vaporization temperature of the oil 118, such as in a vaporizer or by way of another heating device. Such a process can, but need not, include carbonization or burning of at least a portion of the oil and, in at least one embodiment, preferably does not include carbonization or burning so as to at least partially minimize or eliminate one or more effects of carbonization in, for example, a vaporizer, such as the creation of smoke, carcinogens, undesirable flavor, or other potentially harmful or unwanted properties of a substance(s) in inhalable form. The vaporization temperature or boiling point of oil 118 can depend on the particular type of oil 118 used and/or the desired heating temperature according to an implementation of the disclosure, which can be or include any type of consumable oil and/or corresponding temperature. In at least one embodiment, device 100 can be at least partially resistant to such temperatures, which can include being at least partially resistant of temperatures up to 2000 degrees Fahrenheit or about 2000 degrees Fahrenheit. In at least one embodiment, device 100 can at least partially resist temperatures greater than 2000 degrees Fahrenheit. In at least one embodiment, device 100 need not resist temperatures as great as 2000 degrees Fahrenheit or about 2000 degrees Fahrenheit and can at least partially resist temperatures less than 2000 degrees Fahrenheit, which can include any temperature at or above a boiling or vaporization point of an oil 118 stored in device 100 according to an implementation of the disclosure. In at least one embodiment, device 100 can at least partially resist temperatures of up to 160 degrees Fahrenheit or about 160 degrees Fahrenheit, or of up to 375 degrees Fahrenheit or about 375 degrees Fahrenheit, or another temperature between an ambient temperature and a burning or carbonization temperature of a type(s) of oil(s) 118 according to an implementation of the disclosure, such as a temperature in or near the range of 450-550 degrees Fahrenheit.

For example, in at least one embodiment, device 100 can be configured for use in or with one or more heating devices, such as, for example, one or more of the vaporizers disclosed in Applicants' co-pending U.S. patent application Ser. No. 15/950,083 entitled Vaporizer. In at least one embodiment, device 100 can be configured to withstand one or more temperatures, such as a maximum temperature, of a personal vaporizer or other device for vaporizing. For instance, device 100 can be configured for direct heating by a heat source, such as a laser, flame, resistance heater or another heat source, and can be configured to at least partially resist a maximum temperature of such a heat source. As another example, in at least one embodiment, device 100 can be configured for indirect heating by a heat source, such as by way of being exposed to flowing or stagnant air that has been heated by a heat source such as one or more of those mentioned above (or another type of heat source). In at least one embodiment, device 100 or a portion thereof, such as body 102, can be configured for at least partially maximizing heat transfer, such as, for example, by at least partially maximizing one or more surface areas, which can include a total surface area, in contact with a heat source or one or more mediums heated by a heat source (e.g., air or another fluid(s), a heated surface, etc.).

In at least one embodiment, device 100 can include one or more indicators 120, such as letters, numbers, symbols, or logos, for conveying information to a user. For example, as shown in the illustrative embodiment of FIGS. 1-3, device 100 can include one or more indicators 120 on the top and/or bottom of the device (shown schematically in FIG. 3). In an embodiment having multiple indicators 120, the indicators can be the same or different. In at least one embodiment, one or more indicators 120 can be or include a number or other designation indicating an ideal heating temperature or range of temperatures, such as a corresponding heat setting for a vaporizer or other heating device. As other examples, indicators 120 can be or include warning symbols or can provide an indication of the type or amount of oil or other substance stored in the device.

With continuing reference to the Figures, and particular reference to FIGS. 4-6, another of many embodiments of a device according to the disclosure will be described. Device 200 can be the same as device 100 (or any other device embodiment of the present disclosure) in one, some or all respects but can further include one or more openings 220 therein or therethrough for facilitating or otherwise supporting one or more aspects of device 200 or a use thereof, such as the loading of oil therein and/or the removal of oil therefrom. For example, as shown in the exemplary embodiment of FIGS. 4-6 for illustrative purposes, which embodiment is but one of many, device 200 can include a body 202 having one or more openings 220 and the opening(s) 220 can be or include one or more thru holes. As another example, opening 220 can be or include one or more partial holes or other openings, such as one or more grooves, indentations, dimples, or other voids. Device 200 can be of any size and shape according to a physical embodiment or implementation of the disclosure, and can have any number, size and shape of openings 220, such as round, clover, slotted, sliced, square, rectangular, oblong, irregularly shaped, or otherwise configured holes or fluid paths. In at least one embodiment, one or more openings 220 can provide for a relatively larger exterior (or external) surface area versus an embodiment of a device (100, etc.) without such opening(s), which can include having a relatively larger number of pores 114 (see, e.g., FIGS. 7-8) in fluid communication with an atmosphere 222 wholly or partially surrounding device 200 (or, e.g., a structure abutting all or a portion of device 200), such as for example, one or more pores 114 of surface 224 of opening 220. Such an embodiment can be advantageous in one or more implementations of a device according to the disclosure. For example, the presence of one or more openings 220 can allow a heated fluid, such as air or another fluid, to contact or at least partially pass into or through at least a portion of body 202, which can facilitate or otherwise support heating and/or cooling of device 200, such as by way of faster, more even, or more efficient heat transfer to and/or from body 202. As another example, the presence of one or more openings 220 can allow oil to contact or at least partially pass into or through at least a portion of body 202, which can facilitate or otherwise support loading or unloading of device 200, such as by way of faster, more even, or more efficient transfer of oil into or out of body 202.

While the exemplary devices 100, 200 of FIGS. 1-6 are shown to have six radially exterior sides 108 (i.e., to be hexagonal) for purposes of illustration and explanation, these are but two of many examples of configurations for devices according to the disclosure. Devices 100, 200 can include any number of sides 108 (which can include one or more tops 104 and/or bottoms 106), surfaces 110, vertices 112 (if present), openings 220 (if present), indicators 120 (if present), and/or shapes according to an implementation of the disclosure. For example, in at least one embodiment, one or more devices 100, 200 can be sized and shaped for fitting at least partially within or otherwise cooperating with one another or one or more other devices or portions thereof, such as a personal vaporizer or other heating device, a portion of a heating device such as a housing, bowl, chamber, heater, or vaporizable material holder, or a container configured for holding one or more devices 100, 200 separately or in combination when not in use in a vaporizer (e.g., a storage container or transport container). As another example, in at least one embodiment, one or more devices 100, 200 can be sized and shaped for holding an amount of oil, such as a prescribed volume or weight of oil, which can be any amount of oil according to an implementation of the disclosure. For instance, in at least one preferred embodiment, which is but one of many, one or more devices 100, 200 can be sized and shaped for holding an amount of oil between 0.001 milligram (mg) and 1 gram (g) (inclusive), or less, or more, such as at least about 0.05 mg per device, 0.025 mg per device, 0.075 mg per device, 0.1 mg per device, 0.05 g per device, 0.025-0.075 g per device, or another amount, which can be any amount according to an implementation of the disclosure. As another example, in at least one embodiment, one or more devices 100, 200 can be sized and/or shaped and/or otherwise configured based on a number of desired doses or uses according to an implementation of the disclosure, such as one, two, three, or up to fifty or more doses, and can be disposable, replaceable and/or recyclable after use. In at least one embodiment, device 100, 200 can be adapted to have a thermal mass for providing enough heat energy to vaporize or facilitate vaporization of at least a portion of the oil content of the device or a portion thereof upon heating.

As yet another example, in at least one embodiment, one or more devices 100, 200 can be configured for incorporation into a cartridge 300 (see, e.g., FIG. 9) for holding oil and/or cooperating with a heat source for vaporization of oil, which can include being sized and shaped for coupling with a reservoir 302, such as a storage space, housing, tank, or chamber for holding oil to be vaporized during use of or with a vaporizer. Reservoir 302 can have any size, shape, or volume according to a particular application or physical embodiment of the disclosure. In at least one embodiment, which is but one of many, reservoir 302 can have a volume sufficient to hold one gram of oil, but that need not be the case, and reservoir 302 can have a volume for holding more or less than one gram of oil, such as between zero grams and one gram of oil, or more than one gram of oil, such as between one and one hundred grams of oil, or more. In at least one embodiment, which is but one of many, reservoir 302 can be at least generally cylindrical or tubular and can have a diameter of about ¼ inch and a length of about 1 inch. However, that need not be the case, and reservoir 302 can have any size or shape, which can include a size based on desired volume or a shape based on compatibility with one or more vaporizers or components thereof. One or more devices 100, 200 can have a shape similar to, the same as, or different from reservoir 302. One or more devices 100, 200 can be coupled to a reservoir 302 in any manner according to an implementation of the disclosure and at least a portion of a device 100, 200 can be disposed in fluid communication with oil 118 within reservoir 302. As shown in FIG. 9 for illustrative purposes, a cartridge 300 according to the disclosure can include a device 100, 200 coupled to or near an end 306 of reservoir 302. However, this need not be the case and alternatively, or collectively, cartridge 300 can include one or more devices 100, 200 coupled to any portion of reservoir 302. The coupling can occur in any manner according to an implementation of the disclosure, which can include utilization of one or more fasteners, adhesives, seals, gaskets or, as another example, a housing or holder (not shown) coupled to reservoir 302 (e.g., to or about end 306)

and configured to hold one or more devices 100, 200 relative thereto. In at least one embodiment, which is but one of many, device 100, 200 can be pressed into reservoir 302 (or a structure coupled to reservoir 302) and retained in place by interference fit or friction fit. Device 100, 200 can be configured to draw or pull oil from reservoir 302, such as by capillary action and, in at least one embodiment, cartridge 300 can include one or more plugs 308, such as an elastomeric or other float or stopper, configured to sealingly engage the interior surface of reservoir 302 and slide along the interior surface (e.g., toward end 306) as oil is removed from reservoir 302 via device 100, 200. For example, plug 308 can be configured to at least partially prevent oil 118 within reservoir 302 from moving in a direction away from device 100, 200. In other words, plug 308 can be configured to at least partially bias oil 118 within reservoir 302 into or toward contact with device 100, 200. In at least one embodiment, plug 308 can be configured to float in or otherwise at least partially resist sinking into oil 118 within reservoir 302, which can in at least some cases at least partially minimize or prevent leaking of oil 118 from reservoir 302. In at least one embodiment, plug 308 can be configured to at least partially float on or in oil 118 within reservoir 302. In at least one embodiment, plug 308 can be configured to at least partially resist movement in a direction toward oil 118 in reservoir 302, such as by being coupled with reservoir 302 by friction fit, interference fit, or the like. Device 100, 200 can, but need not, be of the same or a similar shape as reservoir 302 and/or plug 308, separately or in combination, in whole or in part.

While exemplary embodiments of device 100, 200 are shown in FIGS. 1-9 for purposes of illustration and explanation, such embodiments are but some of many and numerous other shapes, sizes and configurations of device 100, 200 and/or cartridge 300 are possible. For example, in at least one embodiment, device 100, 200 can be disc- or puck-shaped (see, e.g., FIGS. 9-11), which can include being at least partially cylindrical and/or having an at least partially arcuate or otherwise curved or contoured exterior surface 110. As other examples, device 100, 200 can be pill-shaped, or another shape, such as square, cubical, pentagonal, hexagonal, octanol, oblong, football-shaped, diamond-shaped, double diamond-shaped, star-shaped or any other shape, including irregularly shaped (see, e.g., FIGS. 10-11). FIGS. 10-11 include one or more examples of the shapes mentioned above along with some of many other exemplary embodiments of device 100, 200. The exemplary embodiments of device 100, 200 shown in FIGS. 10 and 11 are labeled with reference numerals 400a, 400b, 400c, et seq. (and may be collectively referred to herein as device(s) 400) for convenience of reference and can include any of the structural and functional aspects of the disclosure described with reference to devices 100, 200, etc. For example, regardless of shape, any of devices 400, in at least one embodiment, can include one or more openings 220 therein or therethrough (see, e.g., embodiments 400aa, 400bb). Alternatively, or collectively, regardless of shape, any of devices 400, in at least one embodiment, can include one or more wholly or partially raised borders (see, e.g., embodiment 400ff), such as on one or more sides or other portions, which can, but need not, at least partially surround an indicator 120, such as a logo, warning, symbol, or other item or designation formed or otherwise disposed on one or more portions of the device (see, e.g., FIGS. 1-3). Any of devices 100, 200, etc., can include one or more indicators 120 absent any border as well. Any of the features and options described here or elsewhere in the present disclosure with reference to device 100, device 200 or another device or embodiment (300, 400, etc.), whether alone or in combination with one or more other embodiments, can apply and be implemented in the same or a similar manner unless otherwise indicated. While numerous configurations of devices 100 (200, 300, et seq.) are illustrated in the Figures, such configurations have been shown for illustrative and explanatory purposes and are not limitative; numerous other shapes, sizes and configurations of the devices of the present disclosure are possible.

With continuing reference to the Figures and specific reference to FIG. 12, one or more methods and/or method steps according to the disclosure will now be described in further detail. One or more devices 100, 200, et seq. (hereinafter collectively referred to as "device(s) 100") can be individually or collectively loaded 502 with oil 118 for subsequent removal of at least a portion of the oil by heating or vaporization, which also can take place individually or collectively. Loading 502 can include one or more of a number of steps and can including filling device(s) 100 wholly or partially. In at least one embodiment, loading 502 can include, but is not limited to, disposing device(s) 100 at least partially in or in contact with oil 118, causing or allowing device(s) 100 to absorb a vaporizable substance by capillary action, immersing device(s) 100 in a vaporizable substance, immersing device(s) 100 in a mixture of a vaporizable substance and one or more non-absorbent media or other media, heating device(s) 100, heating one or more vaporizable substances, condensing, vaporizing or melting one or more vaporizable substances, tumbling device(s) 100 in a vaporizable substance, lowering the viscosity of a vaporizable substance, applying pressure to device(s) 100, subjecting device(s) 100 to a vacuum, evacuating air or other fluids from device(s) 100, mixing device(s) 100 in or with a vaporizable substance, metering or otherwise feeding a vaporizable substance on to or otherwise into contact with device(s) 100, disposing device(s) 100 in a chamber, such as a heated chamber, pressure vessel, oven, vacuum oven, kiln, or other space, disposing device(s) 100 in a mixer, mixing container, tumbler, agitator, tray, or other loading container, conveying device(s) 100, such as along a conveyor belt or other movement system, wholly or partially submerging device(s) 100 in a vaporizable substance, controlling one or more levels, volumes, or amounts of a vaporizable substance, controlling temperature, controlling contact time, and/or controlling viscosity of a vaporizable substance, separately or in combination, in whole or in part, simultaneously or at different times. Any of the foregoing loading 502 steps and/or the other method steps of the present disclosure can occur in any combination or order according to an implementation of the disclosure. In at least one embodiment, loading 502 can include cleaning, scrubbing, washing, bathing, drying, tumbling (alone or with one or more other materials), or otherwise removing one or more substances (which can, but need not, include a vaporizable substance) from one or more devices 100, in whole or in part.

In at least one embodiment, a method of loading 502 one or more devices 100 can include one or more of the following steps: mixing or otherwise combining one or more distillates, such as cannabis oil distillates, with shatter, live resin, or one or more other cannabis extracts, reducing a concentration of tetrahydrocannabinolic acid (THCA), increasing a THC content, consolidating extract in a container, calculating an amount of distillate to combine with an amount of extract, such as, for example, to attain an 80/20 mix of extract and distillate, respectively, warming at least one of an extract and a distillate, such as to a temperature in the range of about 160-200° F., combining and/or mixing one or more calculated or other amounts of distillate and extract, such as for one or more times in the range of about 10-15 minutes and/or at a temperature in the range of about 180-240° F. and/or until at least partially homogenized, transferring one or more components or mixtures into one or more containers, applying an amount of heat sufficient to at least partially melt one or more components, dissolving one or more TCHA crystals, limiting an amount of heat, temperature and/or time for at least partially minimizing or avoiding terpene loss, measuring oil or oil components, counting devices, matching an amount of oil with a number of devices, warming oil, warming devices, warming oil and devices in separate containers and/or to different temperatures, warming oil to a temperature less than or greater than or equal to a temperature to which devices are warmed, warming oil to about 180° F., warming devices to about 225° F., combining devices and oil, pouring devices into oil, pouring oil into devices, stirring mixture of oil and devices one or more times, heating or preheating an oven or vacuum oven, such as to a temperature of about 200° F., disposing oil and/or devices or a mixture thereof in an oven, heating oil and/or devices to about 200° F., subjecting oil and/or devices to a vacuum, such as a vacuum of about 25 inches of mercury (inHg), subjecting oil and/or devices to a vacuum a plurality of times, releasing oil and/or devices from a vacuum a plurality of times, stirring oil and/or devices during or after being subject to a vacuum, separating one or more devices from oil and/or one another, cleaning one or more devices, absorbing oil from an exterior of one or more devices, adding one or more devices to a remainder of a portion of oil, rolling one or more devices, weighing one or more devices, such as filled devices, determining a remaining amount of oil, determining a number of devices to combine with one or more remaining amounts of oil, measuring one or more temperatures, inspecting for one or more characteristics or attributes, such as for the presence of THCA crystals, and repeating one or more of the foregoing steps, separately or in combination, in whole or in part, and in any order.

Device(s) 100 can be individually or collectively stored 504 in one or more containers, which can be or include any type of container according to an implementation of the disclosure. Device(s) 100 can be individually or collectively disposed 506 in a vaporizer or other heating device. Device(s) 100 can be individually or collectively heated 508 to one or more temperatures, such as one or more temperatures sufficient to vaporize at least a portion of the oil 118 within device(s) 100. Vapor emanating from device(s) 100 can be inhaled 510 by one or more users. At least a portion of the oil 118 within device(s) 100 can be depleted 512 over time, which time or time period can vary depending on, e.g., frequency of use and heating temperature. Device(s) 100 can be disposed of 514 after use, which can include discarding device(s) 100 or, in at least one embodiment, recycling device(s) 100 for refilling and reuse.

In at least one embodiment, a method of containing, storing, transporting and/or releasing a vaporizable substance (e.g., oil 118), such as for vaporization, can include loading a device 100 or portion thereof, such as a porous body 102, at least partially with a vaporizable substance and storing the body. In at least one embodiment, loading a device 100 or body 102 can include at least one of causing the body to absorb a vaporizable substance by capillary action, immersing the body in a vaporizable substance, immersing the body in a mixture of a vaporizable substance and a non-absorbent medium, heating the body, heating a vaporizable substance, condensing a vaporizable substance, tumbling the body in a vaporizable substance, lowering the viscosity of a vaporizable substance, applying pressure to the body, subjecting the body to a vacuum, evacuating air from the body and a combination thereof. A plurality of devices 100 or bodies 102 can be loaded simultaneously or otherwise. A method can include heating at least a portion of one or more devices 100 or bodies 102 to a vaporization temperature of a vaporizable substance.

In at least one embodiment, a method of containing, storing, transporting and/or releasing a vaporizable substance, such as for subsequent vaporization, can include loading a device 100 or body 102 at least partially with a plurality of vaporizable substances (e.g., two or more oils 118 or oil 118 and one or more other substances). In at least one embodiment, at least two of the plurality of vaporizable substances can have different vaporization temperatures. A method can include heating device 100 or body 102 to a temperature that can be greater than or equal to a vaporization temperature of one or more of the plurality of vaporizable substances and less than a vaporization temperature of one or more other of the plurality of vaporizable substances. A method can include heating device 100 or body 102 to a temperature that can be greater than or equal to a vaporization temperature of each of a plurality of vaporizable substances. A method can include filtering at least one component of one or more vaporizable substances, such as into, out of, or within device 100 or body 102. A method can include loading device 100 or body 102 at least partially with a plurality of miscible fluids. A method can include loading device 100 or body 102 at least partially with an indicator fluid. A plurality of device 100 or bodies 102 can be loaded or otherwise processed or utilized simultaneously or otherwise.

A method of storing, administering and/or taking a medication can include storing device 100 or body 102 having a volume of medication (e.g., medicated oil 118) disposed therein, disposing, or instructing a person to dispose, device 100 or body 102 into a device for heating at least a portion of device 100 or body 102, and heating, or instructing the person to heat, device 100 or body 102 by activating the device. A method can include causing or instructing a person to consume at least a portion of a volume of medication disposed within or vaporized (or otherwise removed) out of device 100 or body 102. A method can include causing or instructing a person to inhale at least a portion of a volume of medication from device 100 or body 102 in the form of vapor and/or gas. A method can include storing a plurality of devices 100 or bodies 102, which can include storing a plurality of devices 100 or bodies 102 two or more of which have a different amount of medication (or unmedicated oil) disposed therein, such as, for example, different volumes, masses or weights, which can correspond to different prescriptions, doses or treatments.

In at least one embodiment, a device for storing a vaporizable substance can include a porous body having a top, a bottom and a radially exterior surface, the body can be configured to absorb a volume of liquid and to retain the volume of liquid until at least a portion of the volume of liquid can be vaporized, and the body can be configured to retain its shape and pore volume independently of contact with water. The body can be configured to hold oil, medication or another substance, such as in fluid form, and, when heated to an applicable temperature, which can include a temperature sufficient to vaporize at least a portion of such substance without causing carbonization, can release at least a portion of such substance in the form of gas and/or vapor.

In at least one embodiment, the device can have an internal volume of pores for holding a prescribed amount (e.g., by weight, mass, volume or another measure) of fluid and can be configured to vary in one dimension (e.g., thickness) to accommodate one or more amounts of fluid without varying in one or more other dimensions or shapes. At least a portion of the body of the device can be solid or can comprise a solid. In at least one embodiment, at least one of the body's shape, pore size, pore volume and a combination thereof can be fixed.

In at least one embodiment, a liquid stored within the device can have a vaporization temperature and the body or device can have a melting or burning temperature, and the melting or burning temperature can be greater than the vaporization temperature. A pore size of the body can be varied or otherwise adapted for fluids of different viscosities, which can be or include any viscosity according to an implementation of the disclosure. For example, a pore size of the device or a body of the device can be or include a pore size(s) configured for intaking and/or holding by capillary action fluid(s) having a viscosity from about 5 Pa-sec to about 100 Pa-sec at 68 degrees F. or from about 0.5 Pa-sec to about 10 Pa-sec at 113 degrees F. The pore size can be varied to handle different viscosities of oil or other fluid. For example, one or more pore sizes described herein can be used for oils falling within the above-mentioned viscosity ranges. In at least one embodiment, the body can include a matrix of pores, such as interconnected pores, and the matrix can be configured for holding one or more fluids in place within the body, such as via capillary action, which can include holding fluid(s) in place within the body while at least partially minimizing or eliminating the existence of fluid on an exterior surface of the body, in whole or in part. In at least one embodiment, the device can be configured to hold fluid(s) within at least a portion of the pores or matrix until any holding force(s) are overcome via the application of thermal heating, such as heating to a temperature sufficient to overcome the capillary action, which can include turning at least a portion of liquid or other fluid in the matrix to gas or vapor.

In at least one embodiment, a device can include a porous body having a plurality of pores that have a pore size from 0.0001 micron to 100 microns, or less, or more. As another example, a device can include a porous body having a plurality of pores that have a pore size of from 0.1 micron to 20 microns. As another example, a device can include a porous body having a plurality of pores that have a pore size of from 0.4 micron to 5 microns. As another example, a device can include a porous body having a plurality of pores that have a pore size of from 0.5 micron to 5 microns. As other examples, a device can include a porous body having a plurality of pores that have a pore size of from 0.5 micron to 3 microns, or of up to 50 microns, such as 15 microns. As another example, a device can include a porous body having a plurality of pores that have one or more of the above-mentioned pore sizes and a particle retention of 0.5 micron, or of from 0.5 micron to 50 microns or so. Such pore sizes can be average pore sizes or, for instance, maximum pore sizes. In at least one embodiment, at least a portion of the body can be composed of at least one of ceramically bonded alumina, thermally fused alumina, fused silicon carbide, fused metallic beads, fused mineral beads, and a combination thereof. In at least one embodiment, at least a portion of the body can be composed of alumina ($Al_2O_3$) and silicone dioxide ($SiO_2$), separately or in combination with one or more other materials. For example, in at least one embodiment, a porous body can include 75-95% alumina and 5-25% silicone dioxide, or 80-90% alumina and 10-20% silicone dioxide, or 85% alumina and 10-15% silicone dioxide, or about 85% alumina and about 10-15% silicone dioxide. In at least one embodiment, a body can include one or more metals or other materials, such as one or more non-toxic metals or other materials (e.g., $TiO_2$, $FE_2O_3$, $Na_2O$, $B_2O_3$, CaO, MgO). In at least one embodiment, a body can include a nominal particle retention of 0.001-1 micron, such as 0.5 micron or about 0.5 micron, a maximum pore diameter of 15 microns or about 15 microns, a porosity of 20-70%, such as 40-50%, a bulk density of 0.001-4 g/cc, such as 2 g/cc or about 2 g/cc, and a modulus of rupture (MOR) of 2000-5000 psi, such as 4000 psi or about 4000 psi. In at least one embodiment, at least a portion of the body can be composed of naturally occurring materials, such as materials that do not need to be fused at relatively high temperatures, for example coral, diatomaceous earth, or porous lava rock, separately or in combination, in whole or in part.

In at least one embodiment, a manufacturing process can include packing, compressing or otherwise combining particles of known size and/or shape into a porous body for holding fluid, such as within one or more internal pores by capillary action. The process can include combining such particles with one or more binding agents, which can include a substance that can be burned off during manufacturing. In at least one embodiment, the process can include combining such particles with one or more materials such as wax or plastic, disintegrating or boiling off at least a portion of such material(s), leaving a matrix to be fused at a higher temperature and fusing the matrix. In at least one embodiment, the process can include combining such particles with a binding agent that may contain material such as wax or polyethylene, heating the device to a fusing temperature of the matrix, turning the binding agent to a gas or burning it away, and preventing contamination of the device, such as by ensuring no ash or other byproducts of the binding agent remain. In at least one embodiment, a binding agent can be or include one or more relatively high temperature melting materials such as a glass powder (e.g., silicone dioxide, also known as silica, silicic acid or silicic acid anydride) that melts at a very high temperature to bond only the contact areas of a matrix. Alternatively, or collectively, a binding agent can include a substance that changes chemically to form a lower fusing temperature material, such as cotton fibers or other materials that decompose to glass particles that go on to fuse a matrix at higher temperatures.

In at least one embodiment, a device can include a porous body configured to at least partially withstand melting at a temperature, such as an ambient or other temperature, of 2000° F. or about 2000° F. A body can be configured to retain a volume of liquid by capillary action, in whole or in part. In at least one embodiment, a device can include an exterior surface, which can include a radially exterior surface having a plurality of flat or planar sides, which can include quadrilateral sides or sides of another shape(s). In at least one embodiment, a device can include one or more openings or holes therein or therethrough, which can expose additional external surface area for heating and/or allow air or other fluids to pass there through. In at least one embodiment, at least a portion of an exterior surface of a body, which can include a radially exterior surface, can be contoured, which can include being concave or convex, separately or in combination, in whole or in part. A body can include a top and a bottom, which can include a top surface and a bottom surface, any of which can be flat, contoured or both.

In at least one embodiment, a device can include a porous body, wherein at least a portion of the body can be configured to change color or reveal an indicator upon being heated to a temperature, such as an indication temperature or another temperature, which can be or include any temperature according to a particular implementation. In at least one embodiment, an indication temperature can be a vaporization temperature of a liquid stored in the device. In at least one embodiment, a device can be white and can show the color of fluid contained in the matrix. In at least one embodiment, a device can be grey, such as a device having a body comprising silicon carbide, and can show a modified or varied color of fluid contained in the matrix. In at least one embodiment, a device can be configured to show a different color after use, which can include showing or otherwise indicating depletion of fluid contained in the body, such as after thermal release as a gas or vapor. In at least one embodiment, a device can be configured to capture unwanted constituents of a fluid that are or were present for purposes of holding a medication or other substance until use of the device, such as in a vaporizer or other heating device. For example, a lower volatility medication(s) can be boiled out and relatively higher boiling point materials used to carry such medication(s) can remain in the matrix.

In at least one embodiment, a device can include a porous body having a matrix of pores of one or more sizes, which can include diameters, major dimensions, minor dimensions, volumes, areas, surface areas, average dimensions, mean dimensions, or other dimensions. In at least one embodiment, a body can include a first plurality of pores having a first pore size and a second plurality of pores having a second pore size. The first and second pore sizes, which can be any pore sizes according to an implementation, can be the same or different, separately or in combination, in whole or in part.

In at least one embodiment, a device can include a porous body having a volume of liquid stored therein. A liquid can be at least one of, but is not limited to, a medication, a carrier fluid, a solvent and a combination thereof. A volume of liquid can include a plurality of liquids having the same or different vaporization temperatures. In at least one embodiment, a device can include a porous body having an outside surface comprising a top surface, a bottom surface and a radially exterior surface. The outside surface can have a first pore size and the device can have an internal pore volume within or interior of the outside surface. An internal volume can have a second pore size. The first pore size can be the same as or different than the second pore size. One or more exterior surfaces can have or include one or more openings, such as openings in one or more pores or portions of a pore, therein or there through. Such surfaces can include one or more of one or more top surfaces, bottom surfaces, radially exterior surfaces and a combination thereof.

In at least one embodiment, a device for storing a vaporizable substance can include a porous body having a top, a bottom and a radially exterior surface. The porous body can be circular, spherical or another shape. For example, a porous body can have a plurality of sides, such as 2, 3, 4, 5, 6, 7, 8, 9, 10 . . . n sides, which can include up to 100 sides, 1000 sides, or more. In at least one embodiment, a side can be flat or about flat and can have a quadrilateral shape or another shape, which can include having more or less than four sides. In at least one embodiment, a body can have or include any cross-sectional shape shown or described herein and, optionally, can be columnar, which can include having a length or thickness longer than one or more other dimensions, such as a width. In at least one embodiment, a body can be configured to hold an amount of liquid (e.g., oil) until at least a portion of the amount of liquid is vaporized, which can include any volume, weight, mass or other amount of liquid according to an implementation of the disclosure. For example, in at least one embodiment, a body can be configured for holding from about 0.001 milligrams (mg) to at least about 1 gram. In at least one embodiment, a body can be configured for holding 50 mg or about 50 mg. In at least one embodiment, a body can be configured for holding 25-100 mg or from about 25 mg to about 100 mg.

In at least one embodiment, a device for storing a vaporizable substance can include a porous body having a top, a bottom, a plurality of radially exterior sides and a thickness. For example, a body can be hexagonal and can have a thickness of from 0.005 inch to 0.5 inch. As other examples, the body can have a thickness of from 0.09 inch to 0.2 inch, or of from 0.095 inch to 0.16 inch, or of from 0.096 inch to 0.155 inch, or of from 0.096 inch to 0.149 inch. As yet another example, the body can have a thickness of 0.146 inch or about 0.146 inch, or of 0.149 inch or about 0.149 inch. In at least one embodiment, a device for storing a vaporizable substance can include a porous body, such as a hexagonal or otherwise shaped body, having a weight, such as a dry weight, of 0.254 grams, about 0.254 grams, or more, or less. In at least one other embodiment, the body can have a shape other than hexagonal, such as square, pentagonal, heptagonal, octagonal, etc. In at least one embodiment, a device for storing a vaporizable substance can include a porous body having a cross-sectional shape that can remain constant among a plurality of devices configured to hold different amounts of oil or another liquid and a thickness or height that varies according to such amounts. For instance, a thickness can be increased or decreased for holding more or less of a substance, respectively, or vice versa. In at least one embodiment, a device for storing a vaporizable substance can include a porous body having a top with a surface area, a bottom with a surface area, a plurality of radially exterior sides each having a surface area, and a thickness. The surface areas of the top and bottom can be the same or different. The surface areas of two or more sides can be the same or different. The surface area of a side can be less than the surface area of the top and/or bottom. The surface area of a side can be less than half of the surface area of the top and/or bottom. As another example, the combined surface area of two or more sides can be less than the surface area of the top and/or bottom.

In at least one embodiment, which is but one of many, a device for storing a vaporizable substance can include a porous body configured as shown in any of the Figures, wherein thickness t can be within the range from 0.096 inch to 0.155 inch, or from about 0.096 inch to about 0.155 inch. In at least one embodiment, thickness t can be 0.146 inch or about 0.146 inch or, as another example, in or about the range of 0.05 inch to 0.25 inch. As other examples, one or more other dimensions, such as a major dimension, minor dimension, radius, diameter or other dimension, can range from 0.096 inch to 0.155 inch, or from about 0.096 inch to about 0.155 inch. As another example, thickness t and/or any of the other dimensions mentioned above can be less than 0.096 inch, greater than 0.155 inch, or another value, which can be or include any value according to an implementation of the disclosure. Any of the exemplary shapes shown in the Figures (e.g., FIGS. 10-11) for a device for storing a vaporizable substance can have one or more opposite sides or other sides not expressly shown in the Figures hereof and such sides can be the same as or different from the sides that are expressly shown in the Figures hereof. For example, in at least one embodiment of each exemplary alternative (or collective) shape of a device shown in the Figures, the device can be symmetric about one or more planes, which can be any plane, and/or can have one or more opposing or opposite sides that are the same as or mirror one or more sides viewable in the Figures. As other examples, in at least one embodiment of each exemplary alternative shape of a device shown in the Figures, the device can have a cross-sectional shape the same as one or more of its exterior surfaces, such as a top, bottom or other surface, in one or more directions, which can include a direction transverse or perpendicular to such exterior surface. For instance, in at least one embodiment of a device having one of the illustrative shapes shown in, e.g., FIG. 10 or 11, its cross-section can remain the same along at least a portion of, which can include all of, its length or thickness.

Any of the exemplary shapes shown in the Figures (e.g., FIGS. 10-11) for a device for storing a vaporizable substance can, in at least one embodiment, have or include any one or more of the attributes or features illustrated for exemplary purposes in the embodiments of FIGS. 1-9, including, but not limited to, rounded or otherwise shaped corners or edges and/or one or more indicators, symbols, identifiers, letters or numbers thereon or therein. As another example, any one or more of such embodiments can have one or more openings therein or therethrough, such as in a longitudinal or other direction, which can include openings of a circular, oval, oblong, polygonal or other shape, including irregular shapes.

In at least one embodiment, a device for storing a vaporizable substance can include a porous body configured to store oil and to fit within a heating or vaporization chamber of a conventional vaporizer or other heating device. In at least one embodiment, a device for storing a vaporizable substance can include a porous body configured to at least partially minimize contact with a cylindrical, tubular, annular or otherwise shaped heating chamber, such as by way of having one or more points, intersections (e.g., of adjacent sides), scallops or vertices configured to contact the chamber (e.g., an interior surface or portion of the chamber), which can include being configured to allow or route airflow along or proximal to one or more sides, surfaces or other portions of the body, such as within an airflow path in one or more directions in or through a heating device. In at least one embodiment, a device for storing a vaporizable substance can include a porous body having one or more indicators or indications formed thereon or therein, such as, for example, a logo, warning sign, chemical or other substance identifier, thermal setting identifier, temperature identifier, heat identifier, or another indicator(s). Such an indicator can be recessed in a surface of the body, can extend from a surface of the body or, as another example, can be or include a color of the body or a portion thereof.

A device for storing a vaporizable substance can include a porous body having a top, a bottom and an exterior surface. The body can be adapted to absorb a volume of liquid through openings in at least a portion of the exterior surface and to retain the volume of liquid within internal pores until at least a portion of the volume of liquid can be vaporized. A body can be adapted to retain its shape and pore volume independently of contact with water. A device can be adapted to absorb cannabis oil by capillary action. A device can be adapted to retain a volume of cannabis oil within pores interior of the exterior surface of the body. A device can be adapted to retain a maximum weight of cannabis oil, such as 0.05 gram or more or less.

Openings in a body can be at least substantially uniformly disposed about an entire exterior surface of the body. Internal pores of a body can be at least substantially uniformly disposed throughout the entire body. Internal pores of a body can be of an at least substantially uniform pore size. In at least one embodiment, a body can have a pore size of 15 microns and a particle retention of 0.5 micron, or more or less. At least a portion of a body can be a solid. At least one of a body's shape and pore volume can be fixed.

A body can be adapted to at least partially resist melting and/or burning at an ambient temperature of at least 450° F., or more or less. A body can be adapted to retain a volume of liquid by capillary action. An exterior surface of a body can include a radially exterior surface, which can have a plurality of quadrilateral sides. A body can include one or more partial or thru holes. At least a portion of an exterior surface of a body can be concave or convex. A volume of oil can be stored within at least a portion of a plurality of internal pores. A total exterior surface of a body can bound a total body volume. A total body volume can be less than or equal to 0.1 cubic inch, or more.

A device for storing a vaporizable substance can include a porous body having a top, a bottom and one or more sides. A porous body can include a first plurality of pores that comprise openings in an exterior surface of the body and a second plurality of pores disposed wholly or partially within the body. At least a portion of a second or other plurality of pores can be disposed in fluid communication with at least one of a first or other plurality of pores. A porous body can be adapted to take in a volume of oil through openings by capillary action and to retain the volume of oil within one or more of a plurality of pores. A body can be adapted to store or hold oil for vaporization by heating.

A porous body can be adapted to retain its shape and pore volume independently of contact with water or other substances or conditions, including chemicals or temperature. A porous body can be adapted to at least partially resist egress or leakage of oil through exterior openings absent heating or vaporization of the oil. A porous body can be adapted to release or allow release of vaporized oil. A porous body can be adapted to take in and retain liquid cannabis oil. A porous body can be adapted to be heated to a temperature equal to or greater than a vaporization temperature of the cannabis oil. At least one of one or more sides of a porous body can be quadrilateral, or another shape.

A method of storing a vaporizable substance can include disposing one or more devices of the present disclosure in contact with a first volume of oil and removing the device(s) from contact with a remainder of the first volume of oil. Removal can take place after a time period or, for example, after a second or other volume of oil is disposed within a device. A second or other volume of oil can be a portion of a first volume of oil. A method can include storing one or more devices of the disclosure. A method can include at least one of heating one or more devices, heating oil, removing oil from a surface or other portion of a device and a combination thereof. A method can include packaging or otherwise preparing a device of the present disclosure for heating or vaporization of oil within the device.

Other and further embodiments utilizing one or more aspects of the systems and methods described herein can be devised without departing from the spirit of Applicants' disclosure. For example, the devices, systems and methods disclosed herein can be used alone or to form one or more parts of other devices, systems and/or methods, including, but not limited to, vaporizers, vaporizing systems, or methods of vaporizing oil, including but not limited to cannabis oil. Further, the various methods and embodiments of the devices 100, 200, et seq., can be included in combination with each other to produce variations of the disclosed methods and embodiments. Discussion of singular elements can include plural elements and vice-versa. References to at least one item followed by a reference to the item can include one or more items. Also, various aspects of the disclosed embodiments can be used in conjunction with each other to accomplish the goals of the disclosure or the devices, systems or methods of the disclosure.

Unless the context requires otherwise, the words "comprise," "include," and "has" (including variations and conjugations thereof, such as "comprises," "including," "have" and so forth) imply the inclusion of at least the stated element or step or group of elements or steps or equivalents thereof, and not the exclusion of a greater numerical quantity or any other element or step or group of elements or steps or equivalents thereof. The devices, apparatuses and systems can be used in a number of directions and orientations. The order(s) of steps can occur in a variety of sequences unless otherwise specifically limited. The various steps described herein can be combined with other steps, interlineated with the stated steps, and/or split into multiple steps. Similarly, elements have been described functionally and can be embodied as separate components and/or can be combined into components having multiple functions.

The embodiments have been described in the context of preferred and other embodiments and not every embodiment of Applicants' disclosure has been described. Obvious modifications and alterations to the described embodiments are available to those of ordinary skill in the art having the benefits of the present disclosure. The disclosed and undisclosed embodiments are not intended to limit or restrict the scope or applicability of Applicants' disclosures, but rather, in conformity with the patent laws, Applicants intend to fully protect all such modifications and improvements that come within the scope or range of equivalents of the following claims.

What is claimed is:

1. A device for storing a vaporizable substance, the device comprising:
    a porous body having a top, a bottom and an exterior surface;
    wherein the porous body is configured to take in a volume of liquid through openings in at least a portion of the exterior surface and to retain the volume of liquid within internal pores;
    wherein the liquid is cannabis oil;
    wherein the porous body is configured to retain its shape and pore volume independent of contact with water;
    wherein the porous body has a maximum liquid volume, the maximum liquid volume being the maximum volume of liquid the porous body is capable of storing;
    wherein the porous body is configured to retain the maximum liquid volume within the internal pores independent of fluid communication with a source of the liquid; and
    wherein the porous body is configured to be removably and entirely disposed within a vapor chamber of a heating device that heats the porous body for vaporizing at least a portion of the volume of liquid within the porous body.

2. The device of claim 1, wherein the device is configured to retain the maximum liquid volume independent of being removably disposed within the heating device.

3. The device of claim 2, wherein the maximum liquid volume corresponds to a maximum weight of 0.05 gram of cannabis oil.

4. The device of claim 1, wherein the openings are at least substantially uniformly disposed about the entire exterior surface of the porous body, wherein the internal pores are at least substantially uniformly disposed throughout the entire porous body, and wherein the internal pores are of an at least substantially uniform pore size.

5. The device of claim 4, wherein the pore size is a maximum pore size of 15 microns and wherein the device has a particle retention of 0.5 micron.

6. The device of claim 1, wherein the porous body is configured to at least partially resist melting and/or burning at an ambient temperature of at least 450° F.

7. The device of claim 1, wherein the porous body is loaded with the cannabis oil prior to being removably disposed within the heating device.

8. The device of claim 1, wherein the exterior surface of the porous body comprises a radially exterior surface having a plurality of flat sides intersecting at a plurality of points.

9. The device of claim 1, further comprising one or more thru holes in the porous body.

10. The device of claim 1, wherein at least a portion of the exterior surface is concave or convex.

11. The device of claim 1, wherein the exterior surface is the total exterior surface of the porous body and bounds a total body volume, and wherein the total body volume is less than or equal to 0.1 in$^3$.

12. The device of claim 1, wherein the porous body is configured to be utilized with the heating device in the absence of a source of liquid other than the volume of liquid within the porous body.

13. The device of claim 1, wherein the top and the bottom are opposite longitudinal ends, wherein the porous body has a length from the top to the bottom along a longitudinal axis intersecting the top and the bottom and a width perpendicular to the longitudinal axis, and wherein the width of the porous body is greater than the length of the porous body.

14. The device of claim 1, wherein the porous body is ceramic and wherein the device is configured to be the sole source of the vaporizable substance in a vaporizer.

15. The device of claim 1,
    wherein the top and the bottom are opposite longitudinal ends;
    wherein the porous body has a length from the top to the bottom along a longitudinal axis intersecting the top and the bottom;
    wherein the porous body is configured to be selectively disposed in at least first and second positions within the vapor chamber of the heating device during heating; and
    wherein the orientation of the longitudinal axis in the first position differs from the orientation of the longitudinal axis in the second position by 90 degrees.

16. A device for storing a vaporizable substance, the device comprising:
    a porous body configured to take in and retain cannabis oil within internal pores;
    wherein the porous body is solid, such that the shape and the pore vole of the porous body are fixed; and
    wherein the porous body is configured to be removably and entirely disposed within a vapor chamber of a heating device that heats the porous body for vaporizing at least a portion of the cannabis oil within the porous body.

17. The device of claim 16, wherein the internal pores are arranged to provide a maximum particle passage size of less than a pore size of the internal pores.

18. The device of claim 16, wherein the internal pores are arranged such that the cannabis oil flows into the porous body at a first temperature and is retained within the body at a second temperature, the second temperature being lower than the first temperature.

19. The device of claim 16, wherein the porous body has a flat top surface and an opposed flat bottom surface with a longitudinal axis perpendicular to the top and bottom surfaces, wherein the body has a length from the top surface to the bottom surface parallel to the longitudinal axis and a width perpendicular to the longitudinal axis, wherein the porous body includes at least three flat sides arranged around the longitudinal axis, the flat sides intersecting to form at least three points, and wherein the length of the porous body is less than the width of the porous body.

20. A device for storing a vaporizable substance, the device comprising:
- a porous body having internal pores arranged to provide a maximum particle passage size that is smaller than a pore size of the internal pores, the porous body thereby being configured to take in oil at a first temperature and retain the oil within the porous body at a second temperature that is lower than the first temperature;
- the porous body is solid, such that the shape, the pore volume, and maximum particle passage size of the porous body are fixed; and
- wherein the body is configured to release the oil from the porous body when a heating device heats the porous body to a third temperature that is higher than the second temperature.

* * * * *